(12) United States Patent
Rosenberg et al.

(10) Patent No.: US 8,600,500 B1
(45) Date of Patent: Dec. 3, 2013

(54) METHOD AND SYSTEM TO PROVIDE NEURAL STIMULATION THERAPY TO ASSIST ANTI-TACHYCARDIA PACING THERAPY

(71) Applicant: Pacesetter, Inc., Sylmar, CA (US)

(72) Inventors: Stuart Rosenberg, Castaic, CA (US); Taraneh Ghaffari Farazi, San Jose, CA (US); Rupinder Bharmi, Canyon Country, CA (US); Kyungmoo Ryu, Palmdale, CA (US); Edward Karst, South Pasadena, CA (US); Yelena Nabutovsky, Sunnyvale, CA (US); Allen Keel, San Francisco, CA (US); Riddhi Shah, San Jose, CA (US); Fujian Qu, San Jose, CA (US); Ryan Rooke, La Mesa, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/711,504

(22) Filed: Dec. 11, 2012

(51) Int. Cl.
*A61N 1/365* (2006.01)

(52) U.S. Cl.
USPC .................................. 607/15; 607/14

(58) Field of Classification Search
USPC ............................................. 607/15
See application file for complete search history.

(56) References Cited

U.S. PATENT DOCUMENTS

| 5,203,326 A | 4/1993 | Collins |
|---|---|---|
| 7,164,944 B1 | 1/2007 | Kroll et al. |
| 7,228,179 B2 | 6/2007 | Campen et al. |
| 2006/0170486 A1 | 8/2006 | Tranchina et al. |
| 2006/0259098 A1 | 11/2006 | Erickson |
| 2007/0260283 A1 | 11/2007 | Li |
| 2009/0326608 A1 | 12/2009 | Huynh et al. |
| 2010/0036447 A1* | 2/2010 | Zhang et al. ............... 607/4 |
| 2010/0114215 A1 | 5/2010 | Burnes et al. |
| 2011/0106195 A1 | 5/2011 | Kornet et al. |

FOREIGN PATENT DOCUMENTS

| EP | 0547734 B1 | 4/1998 |
|---|---|---|
| WO | 0193953 A1 | 12/2001 |
| WO | 2007133877 A2 | 11/2007 |
| WO | 2007133877 A3 | 3/2008 |
| WO | 2010051385 A1 | 5/2010 |

* cited by examiner

*Primary Examiner* — Michael Kahelin

(57) ABSTRACT

Methods and systems are provided to deliver a neural stimulation (NS) therapy utilizing a first NS operating configuration to assist anti-tachycardia pacing (ATP) therapy in response to a detected tachyarrhythmia. Before and after delivering of the NS therapy, characteristic values are measured for a rate-related physiologic characteristic (rate RPC) and a stability-related physiologic characteristic (stability RPC). The rate RPC is indicative of a frequency of a reentrant circuit within the tachyarrhythmia. The stability RPC is indicative of a hemodynamic stability of the reentrant circuit. The pre-NS and post-NS characteristic values for the rate and stability RPCs are analyzed to determine a rate RPC difference and a stability RPC difference. Different ATP therapies are delivered based on the type associated with the tachyarrhythmia, the rate RPC difference and the stability RPC difference.

24 Claims, 10 Drawing Sheets

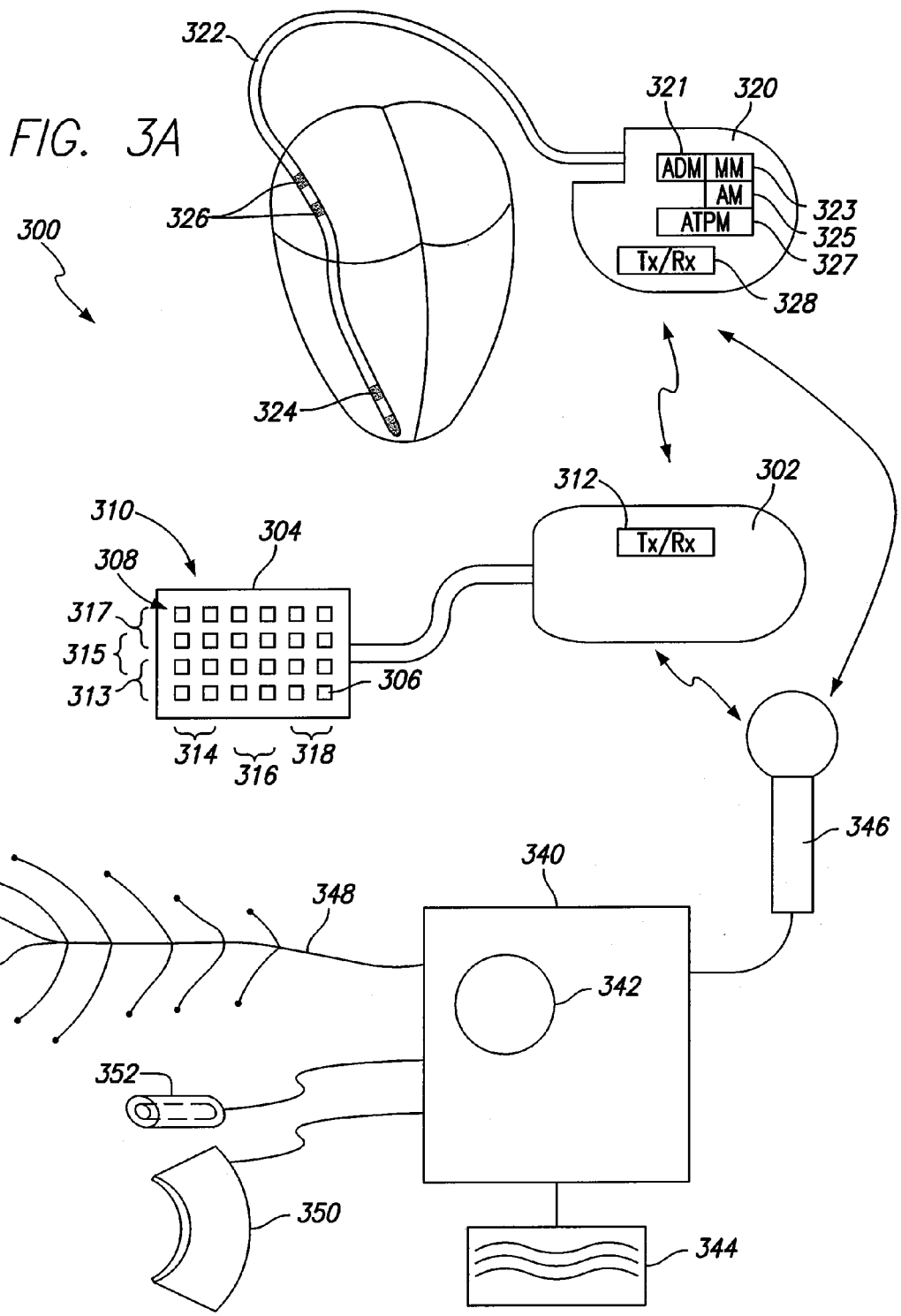

METHOD AND SYSTEM TO PROVIDE NEURAL STIMULATION THERAPY TO ASSIST ANTI-TACHYCARDIA PACING THERAPY

FIELD OF THE INVENTION

Embodiments of the present invention generally relate to neurostimulation systems and methods, and more particularly to assisting anti-tachycardia pacing (ATP) therapy through control of a neurostimulation configuration.

BACKGROUND OF THE INVENTION

Neurostimulation systems (NS) are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

NS and SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In NS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Spinal cord stimulation is commonly used to treat neuropathic pain. More recently, spinal cord stimulation has been considered as a treatment for various cardiac management applications. These may include angina, heart failure (HF), as well as bradycardia and atrial and ventricular tachyarrhythmias including atrial fibrillation (AF).

Literature has discussed the potential to use SCS to suppress bradycardia and tachycardia. Increasing extrinsic neuronal inputs to the intrinsic cardiac nervous system can lead to self-termination of episodes of atrial tachyarrhythmia (AT) and/or fibrillation (AF) in intact hearts without the need for concomitant programmed electrical stimulation of atrial tissue. The proposed electronic and physiologic mechanism to utilize SCS therapy to terminate AF or AT is a complex interaction of sympatholytic and vagotonic signaling.

Many patients implanted with pacemaker or CRT device have prior history of AT and/or AF. In addition, a considerable amount of patients will develop AT and/or AF after device implantation. The pacemaker or CRT device is connected to one or more leads that are implanted or proximate to the heart. The pacemaker or CRT device delivers ATP therapy through the leads directly to cardiac tissue at one or more site(s) of interest. Conventional pacemakers and CRT devices generally operate independently, and without coordination, from other implanted devices such as neurostimulation systems.

More recently, it has been proposed to provide a system that selectively applies ATP therapy and NS therapy. The proposed system initiates an NS therapy to modify a tachyarrhythmia, and initiates ATP therapy to terminate the tachyarrhythmia.

However, a need remains for improved and increased coordination of NS therapy and ATP therapy.

SUMMARY

In accordance with an embodiment, a method is provided to deliver a neural stimulation (NS) therapy to assist anti-tachycardia pacing (ATP) therapy. The method comprises detecting a tachyarrhythmia and identifying a type associated with the tachyarrhythmia, and delivering an NS therapy utilizing a first NS operating configuration. Before and after delivering of the NS therapy, the method measures characteristic values for a rate-related physiologic characteristic (rate RPC) and for a stability-related physiologic characteristic (stability RPC). The rate RPC is indicative of a frequency of a reentrant circuit or focal trigger driving the tachyarrhythmia. The stability RPC is indicative of a spatio-temporal stability of the arrhythmia and/or underlying electrical substrate.

The method analyzes the characteristic values for the rate and stability RPCs for differences, between the rate and stability RPCs, pre-NS and post-NS therapy to determine a rate RPC difference and a stability RPC difference. The method delivers different ATP therapies based on the type associated with the tachyarrhythmia, the rate RPC difference and the stability RPC difference. The rate RPC may represent a frequency of atrial fibrillation (AF) and the stability RPC may represent correlation of RA to LA activation time over multiple cardiac cycles. The rate RPC may represent a frequency of polymorphic ventricular tachycardia (poly VT), and the stability RPC may represent correlation of RV to LV activation time over multiple cardiac cycles. The rate RPC may represent a tachycardia cycle length (TCL) and the stability RPC may represent spatial or temporal dispersion of local activation recovery intervals (ARIs).

The delivery of ATP therapy may include delivering only mono-atrial or specifically RA ATP when the correlation of the RA to LA activation increases post-NS. The delivery of ATP therapy may represent delivering bi-atrial ATP when the frequency of AF decreases and the correlation of the RA to LA activation does not increase. The method may further comprise increasing the NS therapy when the frequency of AF does not decrease and the correlation of the RA to LA activation does not increase.

In accordance with an embodiment, after delivery of the ATP therapy, the method measures updated (post-ATP) characteristic values for the rate and stability RPCs. The method analyzes the updated (post-ATP) characteristic values for the rate and stability RPCs for differences, between the updated characteristic values, pre-ATP and post-ATP therapy to determine a post-ATP rate RPC difference and a post-ATP stability RPC difference. The method delivers at least one of a different ATP therapy and a different NS therapy based on the differences in the post-ATP rate RPC difference and the post-ATP stability RPC difference.

In accordance with an embodiment, the post-ATP rate RPC represents a frequency of atrial fibrillation (AF) and the post-ATP stability RPC represents correlation of RA to LA activation in time. The delivery of ATP therapy includes delivering only mono-atrial (or specifically RA) ATP when the correlation of the RA to LA activation increases. The delivery of ATP therapy represents delivering bi-atrial ATP when the frequency of AF decreases and the correlation of the RA to LA activation does not increase In accordance with an embodiment, the method further comprises increasing the NS therapy when the frequency of AF does not decrease and the correlation of the RA to LA activation does not increase. The characteristic values represent at least one of the following: frequency of AF at RA, frequency of AF at CS/LA, correlation of RA to LA activation time, frequency of PVT at RV, frequency of PVT at one or more LV sites, correlation of activation time at RV and LV sites, tachycardia cycle length (TCL), and local activation-recovery interval (ARI).

In accordance with an embodiment, a system is provided to deliver a neural stimulation (NS) therapy to assist anti-tachycardia pacing (ATP) therapy. The system comprises an arrhythmia detection module configured to detect a tachyarrhythmia and identify a type associated with the tachyarrhythmia, and an NS module configured to deliver an NS therapy utilizing at least a first NS operating configuration. The system further comprises an arrhythmia detection module that is configured to detect a tachyarrhythmia and identify a type associated with the tachyarrhythmia. The system further comprises a measurement module that is configured to measure, before and after delivering of the NS therapy, characteristic values for a rate-related physiologic characteristic (rate RPC) and for a stability-related physiologic characteristic (stability RPC), the rate RPC indicative of a frequency of a reentrant circuit or focal trigger driving the tachyarrhythmia, the stability RPC indicative of a spatio-temporal stability of the reentrant circuit. The system further comprises an analysis module that is configured to analyze the characteristic values for the rate and stability RPCs for differences, between the rate and stability RPCs, pre-NS and post-NS therapy to determine a rate RPC difference and a stability RPC difference. The system further comprises an ATP module that is configured to deliver different ATP therapies based on the type associated with the tachyarrhythmia, the rate RPC difference and the stability RPC difference.

The ATP module may be configured to deliver only mono-atrial (or specifically RA) ATP when a correlation of RA to LA activation increases. The ATP module may be configured to deliver bi-atrial ATP when a frequency of AF decreases and a correlation of RA to LA activation does not increase.

The measurement module may be configured to measure, after delivery of the ATP therapy, post-ATP characteristic values for the rate and stability RPCs. The analysis module may be configured to analyze the post-ATP characteristic values for the rate and stability RPCs for differences, pre-ATP and post-ATP therapy to determine a post-ATP rate RPC difference and a post-ATP stability RPC difference. At least one of the ATP module and the NS module may be configured, respectively, such that the ATP module delivers a different ATP therapy and the NS module delivers a different NS therapy based on the differences in the post-ATP rate RPC difference and the post-ATP stability RPC difference.

BRIEF DESCRIPTION OF THE DRAWINGS

FIG. 3A illustrates a block diagram of an exemplary system that may be implemented in accordance with an embodiment.

DETAILED DESCRIPTION

Figure 1:
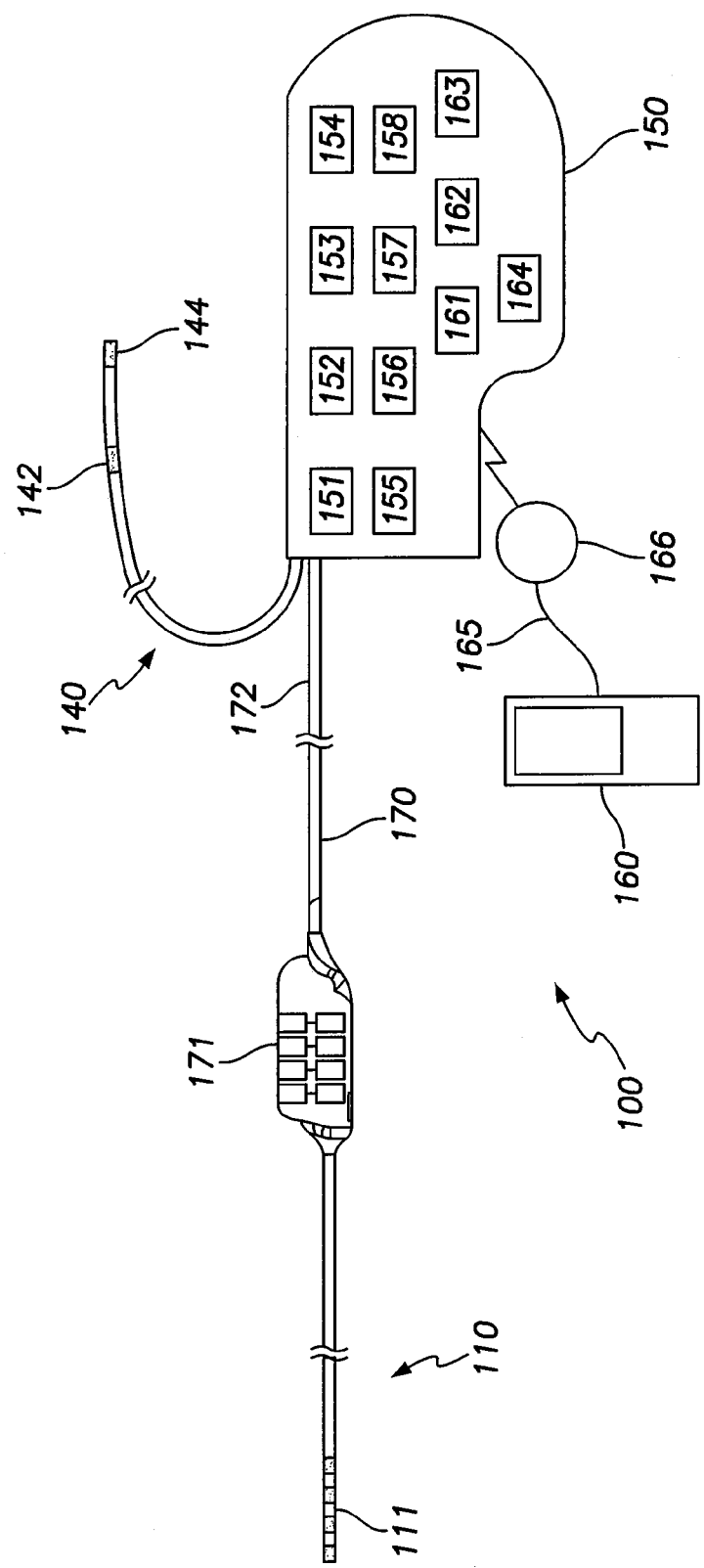
FIG. 1 depicts a neurological stimulation system that generates electrical pulses for application to nervous tissue of a patient according to one embodiment.

Embodiments described herein include systems and methods that utilize neural stimulation (NS) therapy to assist anti-tachycardia pacing (ATP) therapy. NS therapy, such as spinal cord stimulation, modulates the balance of autonomic tone, reducing sympathetic drive and/or increasing parasympathetic activation. Additionally, it has been shown that NS therapy prolongs atrial effective refractory periods, and enhances the repolarization changes in response to direct vagal stimulation. NS therapy, such as spinal cord stimulation, is achieved by a multi-electrode lead implanted in or along the epidural space and connected to a pulse generator. The selection of electrode configuration, frequency, pulse width, and stimulus intensity are all controllable/programmable parameters. In accordance with embodiments, logic is provided within the NS pulse generator that allows automatic turning ON or OFF of the stimulation and also automatic adjustment of stimulation parameters based on previously-programmed setup by the clinician; further, the turning ON/OFF and parameter adjustment is triggered by an implantable cardiac device, by one of combination into the same device (CRM+SCS in a can), direct connection, or wireless communication between the devices.

In embodiments herein, spinal cord stimulation is turned on by a trigger of tachycardia detection in either the atrium or ventricle. NS therapy can be delivered beginning the moment the IMD enters the decision tree for tachyarrhythmia detection and discrimination, or may be turned on at specific times after some failed attempts at ATP, as will be described in specific embodiments. Embodiments use NS therapy to shorten the excitable gap of a reentrant tachycardia so that it self-terminates. Alternately, embodiments use different NS parameters to lengthen the excitable gap to allow greater penetration into the reentrant circuit by a pulse train for entrainment.

Embodiments use NS therapy to decrease heterogeneity of electrophysiology (EP) substrate, thereby organizing a complex tachyarrhythmia and making it more amenable to pace termination. Similarly, embodiments use NS therapy to change the EP substrate to slow down a fast tachyarrhythmia, making it more amenable to pace termination. Embodiments turn on NS therapy during a hemodynamically unstable arrhythmia to slow the tachycardia cycle length, converting it to a hemodynamically stable arrhythmia. Embodiments utilize NS electrode configurations specifically determined based on mapping at implant, in order to selectively affect regions of the heart in order to steer a function reentrant circuit toward the direction of an implanted pacing electrode, enabling better penetration of pulse trains. Upon failed conventional ATP, embodiments are provided that ramp up NS parameters along with pacing parameters to increase the probability of success at subsequent ATP attempts. Certain embodiments leverage simultaneous or triggered offset (i.e. cessation) of both ATP and NS to modulate EP substrate at precisely the time of causing a reentrant wavefront to collide with the last stimulus in a pulse train.

In addition to facilitating ATP effectiveness, using NS therapy to modulate the underlying substrate can also enhance the efficacy of lower-energy cardioversion or defibrillation shocks. This is advantageous in cases where clinicians program low energy shocks instead of ATP as the first therapy to deliver. The mechanism by which this operates is similar. NS promotes organization of a more complex arrhythmia by way of modifying refractoriness and conduction velocity, so that a shock that would otherwise have too little energy to completely reset a complex tachyarrhythmia does have sufficient energy to terminate this less complex one.

FIG. 1 depicts a neurological stimulation system 100 that generates electrical pulses for application to nervous tissue of a patient according to one embodiment. For example, system 100 may be adapted to stimulate spinal cord tissue, peripheral nerve tissue, deep brain tissue, cortical tissue, or any other nervous tissue within a patient's body.

System 100 includes implantable NS device 150 that is adapted to generate electrical pulses for application to the nerve system of a patient. Implantable NS device 150 typically comprises a metallic housing that encloses controller 151, pulse generating circuitry 152, battery 153, recharging circuit 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the NS device 150 for execution by the microcontroller or processor to control the various components of the device.

The NS device 150 may comprise a separate or an attached extension component 170. If extension component 170 is a separate component, extension component 170 may connect with the "header" portion of NS device 150. If extension component 170 is integrated with NS device 150, internal electrical connections may be made through respective conductive components. Within NS device 150, electrical pulses are generated by pulse generating circuitry 152 and are provided to switching circuitry 157. The switching circuit connects to outputs of NS device 150. Electrical connectors (e.g., "Bal-Seal" connectors) within connector portion 171 of extension component 170 or within the NS DEVICE header may be employed to conduct the stimulation pulses. The terminals of one or more stimulation leads 110 are inserted within connector portion 171 or within the NS DEVICE header for electrical connection with respective connectors. Thereby, the pulses originating from NS device 150 are provided to stimulation lead 110. The pulses are then conducted through the conductors of lead 110 and applied to tissue of a patient via electrodes 111. Any suitable known or later developed design may be employed for connector portion 171.

For implementation of the components within NS device 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within NS device 150. Different pulses on different electrodes may be generated using a single set of pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may comprise a lead body of insulation material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

The NS device 150 includes one or more inputs 161 that are configured to receive cardiac signals. A sensing lead 140 is connected to the NS device 150. The sensing lead 140 collects cardiac signals from a patient and supplies the cardiac signals to the inputs 161. Optionally, the inputs 161 may also receive cardiac signals from a separate implantable device and/or from an external device. The cardiac signals are representative of cardiac rhythms experienced by the patient over a period of time and in connection with multiple NS configurations. For example, an external device (e.g. ICD) may send a signal representing a reduced information set of characteristics of cardiac rhythms. For example, the signal received at input 161 may represent a control signal containing the type of rhythm/arrhythmia encoded, along with the instantaneous rate, etc. The sensing lead 140 includes sensors 142 and 144 that sense cardiac activity and generate cardiac signals associated therewith. As one example, the sensors 142, 144 may sense IEGM signals. Optionally, the sensing lead 140 may sense ECG signals, heart sound signals, blood pressure signals, blood oxygen content signals and the like.

The NS device 150 may include a cardiac arrhythmia analysis (CAA) module 158 that analyzes cardiac signals to identify the occurrence of an arrhythmia. For example, the CAA module 158 may detect onset and/or termination of various arrhythmias such as atrial fibrillation (AF), atrial flutter (AFL), atrial tachy-cardia (AT), ventricular fibrillation (VF), polymorphic VT, monomorphic VT, ventricular tachycardia (VT), ST segment shift, and the like. Alternatively, the NS device 150 may receive a communication from an external device or another implantable device indicating that onset of an arrhythmia has been detected, an AT has changed to AF, AF has changed to AFL, an arrhythmia has been terminated and the like. For example, the NS device 150 may receive the communication from an implantable pacemaker, ICD, CRT, defibrillator, CRM device and the like. Optionally, the NS device 150 may receive the communication from an external home monitor, external programmer, external ECG monitor and the like. Optionally, the controller 151 may be configured to direct the NS device 150 to begin operation in a select one of the NS configurations in response to a determination that the cardiac rhythm exhibits an arrhythmia. The select NS configuration may be preprogrammed or based on the type of arrhythmia detects.

The NS device 150 includes memory 164 that is configured to save multiple NS configurations. The memory 164 maintains a one to one relation between the characteristic values that are derived and a one of the NS configurations that was operative at the time when the cardiac signals associated with the characteristic values were collected.

The NS device 150 includes a cardiac signal analysis (CSA) module 162 that is configured to derive, from the cardiac signals, characteristic values (CVs) for at least one physiologic characteristic indicative of at least one of normal and abnormal cardiac rhythms that occur while the NS device operates, at different time intervals, in at least the sub-set of the multiple NS configurations. The CSA module 162 determines a characteristic value for at least one of an acute cardiac rhythm characteristic and a chronic cardiac rhythm characteristic. The CSA module 162 determines a characteristic value for at least one of the following physiologic characteristics: restoration time, R-R interval, P-P interval, R-wave regularity, P-wave regularity, dominant frequency of atrial fibrillation (AF), AF rate, AF regularity, Peak atrial rate, and a ratio of a number of ventricular events per set of atrial events.

The NS device 150 also includes a CV analysis module 163 that is configured to analyze the CVs and select, from the multiple NS configurations, an NS operating configuration to be used by the NS system based on the characteristic values. The CV analysis module 163 identifies a select characteristic value that satisfies a predetermined condition and determines a one of the NS configurations that is associated with the select characteristic value.

The controller 151 changes the NS configuration by switching between at least one of i) first and second electrode combinations, ii) first and second stimulus patterns, and iii) first and second active electrode placements, utilized to delivery an NS therapy from the NS lead. Optionally, the controller 151 may change the NS configuration by switching between first and second stimulus patterns utilized to delivery an NS therapy from the NS lead. As one example, one of the first or second stimulus patterns could be "stimulus OFF". Hence, when an the IMD may identify a characteristic value for a physiologic characteristic(s) of interest and in response thereto trigger the NS device to switch from being inactive and monitoring to being active and delivering therapy. Optionally, the controller 151 may change the NS configuration by changing a configuration value of at least one configuration parameter from the set of configuration parameters that includes stimulus phase, frequency, pulse width, pulse amplitude, number of active electrodes, active electrode pattern, active electrode position within electrode array, active electrode placement with respect to a reference anatomy. The controller 151 changes from one of the NS configurations to another NS configuration based on at least one of i) automatically after a predetermined of time and ii) the physiologic characteristic of the cardiac signals, the physiologic characteristic representing AT/AF burden, the memory recording the characteristic values for AT/AF burden exhibited during each of the predetermined periodic intervals.

Figure 2C:
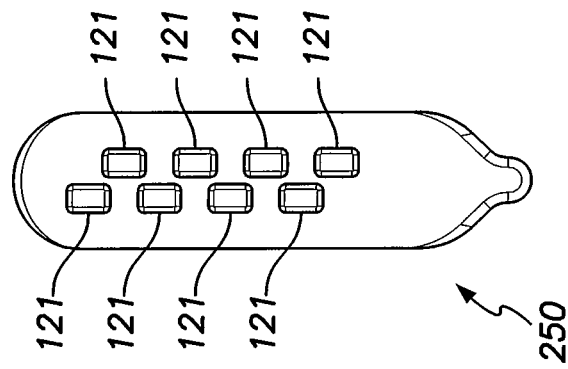
FIGS. 2A-2C respectively depict stimulation portions for inclusion at the distal end of a lead according to various embodiments.
Figure 2B:
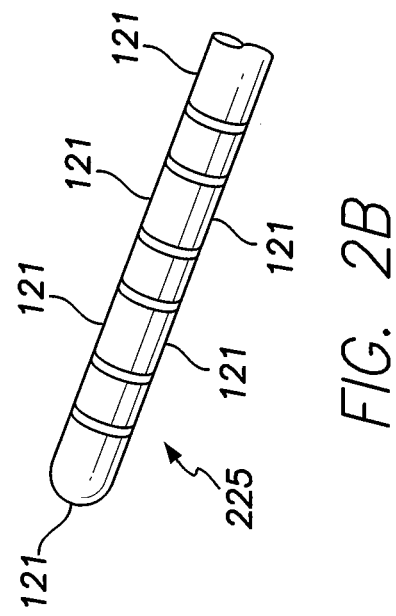
Figure 2A:
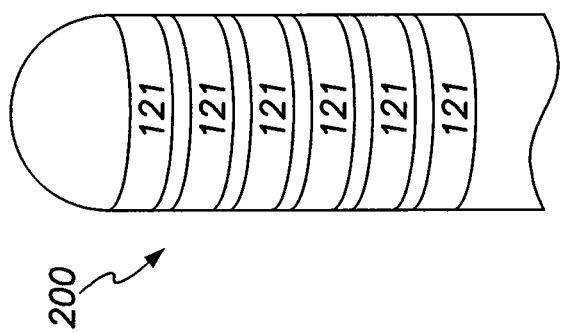

FIGS. 2A-2C illustrate stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes"121. The term "segmented electrode" 121 is distinguishable from the term "ring electrode." As used herein, the term "segmented electrode" refers to an electrode 121 of a group of electrodes 121 that are positioned at the same longitudinal location along the longitudinal axis of a lead and that are angularly positioned about the longitudinal axis so they do not overlap and are electrically isolated from one another. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

Controller device 160 may be implemented to battery 153 of NS device 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown).

The patient then places the primary coil 166 against the patient's body immediately above the secondary coil (not shown), i.e., the coil of the implantable medical device. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to battery 153 by recharging circuit 154. Recharging circuit 154 may also communicate status messages to controller 160 during charging operations using pulse-loading or any other suitable technique. For example, controller 160 may communicate the coupling status, charging status, charge completion status, etc. Optionally, the controller 160 may operate as a "relay" by receiving cardiac signals from a separate implantable device and/or an external device and relaying/conveying the cardiac signals to the NS device 150.

External controller device 160 is also a device that permits the operations of NS device 150 to be controlled by user after NS device 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with NS device 150.

Controller device 160 preferably provides one or more user interfaces to allow the user to operate NS device 150. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 160 may permit operation of NS device 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. The NS device 150 modifies internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

FIG. 3A illustrates a block diagram of an exemplary system 300 that may be implemented in accordance with an embodiment. The system 300 includes an NS device 302 that is coupled to an NS lead 304. As one example, the NS lead 304 includes electrodes 306 that are arranged in a two dimensional array of rows 308 and columns 310. The electrodes 306 delivery NS therapies based on the current operating NS configuration. Optionally, other NS lead configurations may be used.

The NS device 302 will activate different combinations of the electrodes 305, such as to electronically shift a placement where and configuration at which an NS therapy is delivered on a particular spinal region. For example, during NS configurations #1, #2 and #3, different electrode column combinations 314, 316 and 318, respectively, may be active. By moving between NS configurations, and thus active electrode column combinations 314, 316 and 318, the NS therapy can be delivered at different lateral or longitudinal positions along the vertebra relative to a lateral reference point. Similarly, the active electrode row combinations 313, 315 and 317 could be switched to shift a position of the NS therapy in a vertical direction up or down relative to a vertical reference point on a vertebra.

A separate implantable medical device (IMD) 320 is provided. The IMD 320 may be a pacemaker, ATP device, ICD device, CRT device, other CRM device such as subcutaneous AF monitor, or other device configured to sense and/or deliver stimulus to cardiac tissue. The IMD 320 is coupled to at least one lead 322 that has a distal end that is configured to be inserted into one or more chambers of the heart. For example, the lead 322 may include a distal end with one or more electrodes 324 inserted into the right ventricle. The lead 322 may also include one or more electrodes 326 located in the right atrium. The lead 322 represents one example and in no way is intended to limit the present invention. Optionally, more or different leads may be included, such as leads with electrodes proximate to the LA and/or LV. The electrodes 324 and 326 sense cardiac signals and may also deliver pacing and/or high voltage stimulus to the heart tissue. The IMD 320 includes a transmitter/receiver (Tx/Rx) 328 that is configured to communicate with the transmitter/receiver (Tx/Rx) 312 in the NS device 302. The Tx/Rx 328 may convey, among other things, cardiac signals sensed at the IMD 320 to the NS device 302. The IMD 320 detects and analyzes the cardiac signals sensed by the electrodes 324, 326 to identify onset, change, and/or termination of an arrhythmia (e.g., AF or VF onset detected, AF or VF start time, AF or VF termination detected, AF or VF end time, AT or VT onset detected, AT or VT start time, AT or VT termination detected, AT or VT end time, ST segment shift and the like). FIGS. 4-7 illustrate various manners by which NS and ATP therapies are coordinated based on different types of arrhythmias that are detected by the IMD 320.

The IMD 320 includes an arrhythmia detection module 321 that is configured to detect a tachyarrhythmia and identify a type associated with the tachyarrhythmia. The IMD 320 includes a measurement module 323 that is configured to measure, before and after delivering of the NS therapy, characteristic values for a rate-related physiologic characteristic (rate RPC) and for a stability-related physiologic characteristic (stability RPC). The rate RPC is indicative of a frequency of an reentrant circuit or focal trigger driving the tachyarrhythmia. The stability RPC is indicative of a spatio-temporal stability of the arrhythmia. The IMD 320 includes an analysis module 325 that is configured to analyze the characteristic values for the rate and stability RPCs for differences, between the rate and stability RPCs, pre-NS and post-NS therapy to determine a rate RPC difference and a stability RPC difference. The IMD 320 further includes an ATP module 327 that is configured to deliver different ATP therapies based on the type associated with the tachyarrhythmia, the rate RPC difference and the stability RPC difference.

The rate RPC may represent a frequency of atrial fibrillation (AF) and the stability RPC represents correlation of RA to LA activation time over multiple cardiac cycles. Optionally, the rate RPC may represent a frequency of polymorphic ventricular tachycardia (poly VT), and the stability RPC may represent correlation of RV to LV activation time over multiple cardiac cycles. Optionally, the rate RPC may represent a tachycardia cycle length (TCL) and the stability RPC may represent the spatial dispersion of local activation recovery interval (ARI) measured at more than one location. The spatial dispersion indicates how the ARI, when measured at multiple sites during a single cardiac cycle or one at a time over several cardiac cycles within a relatively short period of time (e.g. up to a few minutes), varies across different measurement locations. Optionally, the rate RPC may represent a tachycardia cycle length (TCL) and the stability RPC may represent the temporal dispersion of local ARI measured repeatedly at one location over more than one cardiac cycle. The temporal dispersion indicates how the ARI, measured at one location during different beats, differs beat by beat.

The ATP module 327 may be configured to deliver only mono-atrial (specifically, RA) ATP when a correlation of RA to LA activation increases. The ATP module 327 may be configured to deliver bi-atrial ATP when a frequency of AF decreases and a correlation of RA to LA activation does not increase.

The measurement module 323 is configured to measure, after delivery of the ATP therapy, post-ATP characteristic values for the rate and stability RPCs. The analysis module 325 is configured to analyze the post-ATP characteristic values for the rate and stability RPCs for differences, pre-ATP and post-ATP therapy to determine a post-ATP rate RPC difference and a post-ATP stability RPC difference. At least one of the ATP module and the NS module may be configured, respectively, such that the ATP module delivers a different ATP therapy and the NS module delivers a different NS therapy based on the differences in the post-ATP rate RPC difference and the post-ATP stability RPC difference.

The IMD 320 analyzes the cardiac signals to identify characteristic values (CVs) for the physiologic characteristic(s) of interest. For example, the IMD 320 implements a cardiac signal analysis module (similar to the CSA module 162 in FIG. 1) to derive, from the cardiac signals, characteristic values for at least one physiologic characteristic discussed herein. The IMD 320 includes a CV analysis module (similar to CV analysis module 163 in FIG. 1) to analyze the CVs and select, from the multiple ATP therapies.

An external device 340 is shown in FIG. 3A. The external device 340 may be a home monitoring device, a Holter monitor worn by the patient, an external IMD or NS programmer, an ECG monitor and the like. The external device 340 includes a display 342, an input keyboard 344, and an antenna 346 used to communicate with the NS device 302 and the IMD 320. A surface electrode set 348 is joined to the external device 340 to collect ECG signals as cardiac signals. Optionally, a blood pressure cuff 350 and blood oxygen sensor 352 may be coupled to the external device 340 to sense blood pressure and blood oxygen content, respectively. The external device 340 may transmit cardiac signals from the surface electrode set 348, the blood pressure cuff 350 and/or blood oxygen sensor 352 to the NS device 302 through the antenna 346.

The external device 340 may include an arrhythmia detection module, a measurement module, an analysis module and an ATP module (similar to 321, 323, 325, and 327 in the IMD). The external device 340 may implement a cardiac signal analysis module (similar to the CSA module 162 in FIG. 1) to derive, from the cardiac signals, characteristic values for at least one physiologic characteristic indicative of at least one of normal and abnormal cardiac rhythms that occur while the NS device operates. When the external device 340 calculates CVs, the external device 340 may transmit the CVs to the IMD 320 and/or the NS device 302 through the antenna 346.

Optionally, the external device 340 may also include a CV analysis module (similar to CV analysis module 163 in FIG. 1) to analyze the CVs and select, from the multiple NS configurations and ATP therapies. When the external device 340 analyzes CVs to select an ATP therapy or NS configuration, the external device 340 transmits instructions to change the NS operating configuration or ATP therapy and/or each new NS configuration or ATP therapy.

As described herein, an NS device is used to deliver NS therapy. Optionally, the IMD or an external device may be used to deliver ATP therapy as well as NS therapy. Hence, the terms "spinal column stimulus", "SCS" or "NS module" are used herein to collectively refer to any software function, device or system that delivers NS therapy, such as a separate NS device, an IMD configured to deliver NS therapy, an external device configured to deliver NS therapy and the like.

In accordance with embodiments described herein, the NS device or module is turned on in order to increase the refractory period and/or change the conduction velocity of the arrhythmia driver (i.e. reentrant circuit or focal trigger), thereby lengthening the tachycardia cycle length. When the NS device is turned on, during ventricular tachyarrhythmia with unstable hemodynamics, the modulated EP substrate results in a slower VT that is hemodynamically stable. An added advantage of the slower VT is that in addition to providing a longer diastolic period to allow at least nominal ventricular filling, it is also more easily terminated by ATP therapy.

Optionally, the NS device may be utilized to modulate coronary perfusion. By increasing NS therapy during longer duration VTs, there becomes a decreased likelihood of ischemia due to reduced perfusion pressures that would further perpetuate the VT.

In accordance with an embodiment, at implant of the NS device, an invasive cardiac map is assessed to determine the particular regions of the heart affected by specific NS parameters. For example, stimulation at a distal electrode in the spinal cord may be found through mapping to selectively prolong the right atrial refractory period and increase conduction velocity in the left atrial roof, while stimulation at a more proximal electrode in the spinal cord may prolong refractory periods near the pulmonary veins. The NS configurations and target anatomic locations—at least one or more locations of interest, near implanted cardiac leads—are stored in the NS device, IMD and/or external device for later use.

Instead of, or in addition to, ramping the cardiac pacing ATP parameters up/down, the NS parameters may be ramped up/down. For example, the amplitude and/or frequency of the NS therapy may be progressively increased upon ATP failing at a cycle length that is as short as can be safely achieved (for example, 70% of tachy cycle length). By progressively increasing the NS therapy amplitude, myocardium refractoriness is progressively prolonged, effectively decreasing the size of excitable gap and preventing the ATP conducted wave from resetting the reentrant tachycardia cycle.

In one example, the ATP therapy may begin by delivering (in one or both ventricles) ATP pulses utilizing standard parameters (e.g. 85% cycle length (CL)) to condition the myocardium (fully entrained). Then, the method may simultaneously turn on NS therapy to elicit known prolongation of the refractory period, and change the ATP CL to 100% of tachy CL. The combined lengthening of the reentrant tail and the prolonged drive cycle length may result in collision of paced and reentrant wave fronts and the termination of the tachycardia. Furthermore, even for the tachy episodes that fail to terminate with ATP therapy, the introduction of NS therapy during ATP therapy will confer a safety benefit by decreasing the likelihood of acceleration into VT.

Figure 3B:
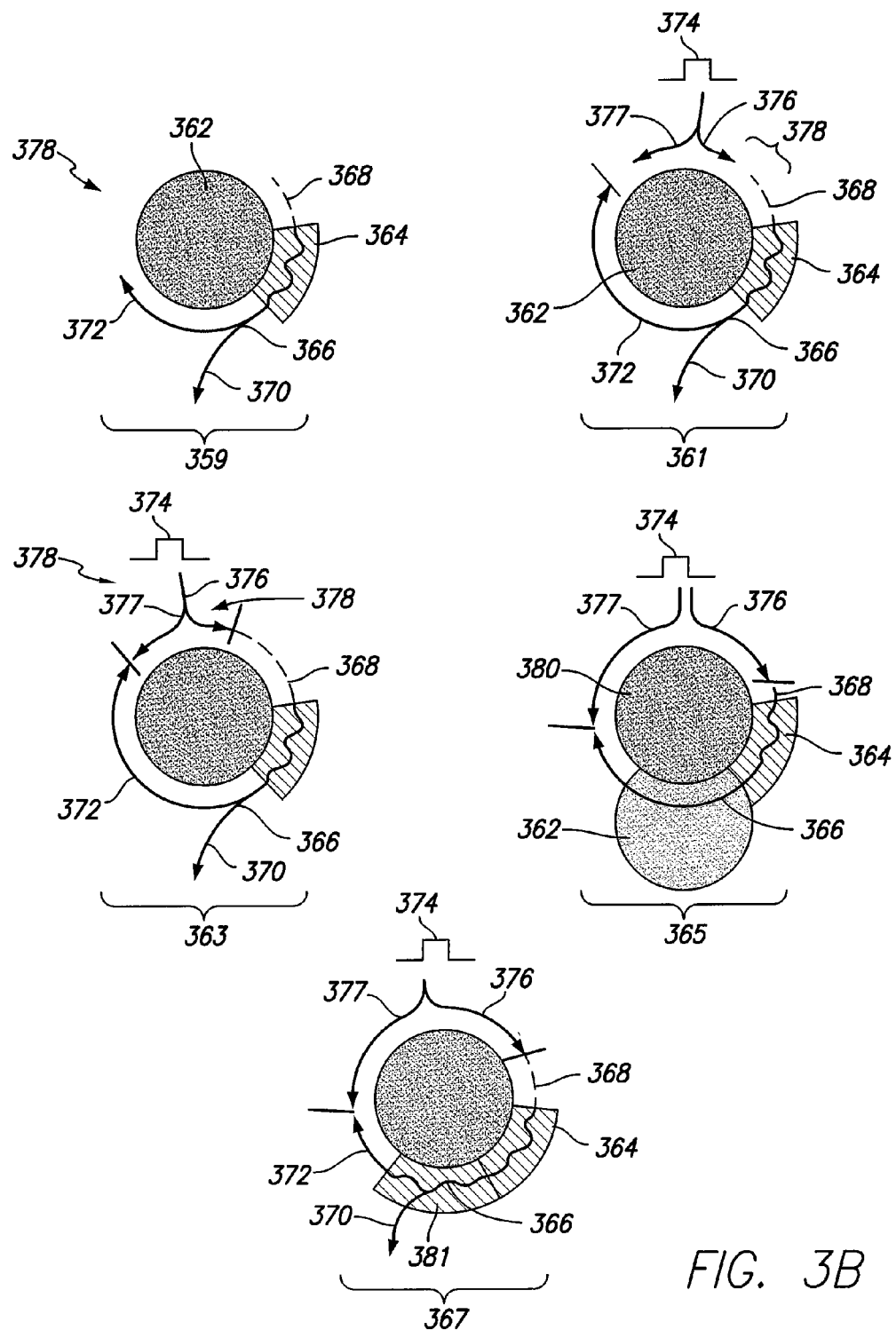
FIG. 3B illustrates graphical representations of exemplary reentrant circuits experienced by the heart.

FIG. 3B illustrates examples of different reentrant circuits 359, 361, 363, 365 and 367 within a region of a chamber in the heart affected in different manners by NS and ATP therapies. The reentrant circuits may be mapped at the time of implant of the NS device 302 and/or the IMD 320 and/or an external cardiac recording/mapping system. The methods and systems described herein may, optionally, be implemented with or without information derived by performing a mapping of the reentrant circuits. For example, an implanted NS device may be used with temporary catheters in the heart with an appropriate electroanatomic mapping system. First, a baseline may be measured for various parameters at many locations on the heart before an NS or ATP therapy is delivered. For example, the parameters may include activation sequence, local activation time, local conduction velocity, local repolarization time, local activation-recovery interval and the like.

Next, a first NS therapy is delivered, while re-measuring the same cardiac parameters in the presence of the first NS therapy. Next, a second different NS therapy may be delivered (etc., for any number of NS configurations). The same cardiac parameters are measured in the presence of the second and subsequent NS therapies. Numerous NS therapies may be delivered and mapped in connection with various types of arrhythmias and reentrant circuits.

The measurements are recorded. Optionally, a lookup table or other mechanism may be used to associate each of the various NS therapy configurations with the anatomic regions of the heart, on which the NS therapy have substantial electrophysiology effects. Of particular interest are zones that are likely to be associated with reentrant tachyarrhythmias, including the anatomic (fixed) isthmuses such as that between IVC and tricuspid valve (for atrial flutter), the area around papillary muscle insertion to LV (reentrant VT), border zones of scar (scar-related VT), etc.

Once, NS therapies are mapped to various EP effects, upon detection of a tachyarrhythmia, the NS configuration can be chosen that is associated with electrophysiology changes to the anatomic region involved in the arrhythmia.

Returning to FIG. 3B, reentrant circuits 359, 361, 363, 365 and 367 are shown that include an anatomical or functional obstacle 362, through which conduction is blocked. A slow conduction zone 364 is shown along one side of the anatomic obstacle 362. Electrical conduction passes through the slow conduction zone 364, however at a slower rate than in normal healthy physiologic tissue. The slower conduction is denoted by a "squiggly" line through the slow conduction zone 364.

The reentrant circuits 359, 361, 363, 365 and 367 illustrate an activation wave 366 as a solid line that travels around the anatomic obstacle 362. The activation wave 366 travels along the right side of the anatomic obstacle and passes through the slow conduction zone 364. The slow conduction zone 364 slows down progress of the activation wave 366, such that the tissue on the opposite (left) side of the anatomic obstacle 362 has already undergone an activation wave, undergone a refractory state, and has reset to become physiologically excitable again. The dashed line represents the refractory tail 368, while the arrow represents the head of the activation wave 366. The distance between the head and tail around the reentrant circuit 359 represent an excitable gap 378, in which tissue is susceptible to excitation.

Once the activation wave 366 leaves the slow conduction zone 364, the activation wave 366 splits into two branches denoted as an activation wave 370 and activation wave 372. The activation wave 370 conducts in the usual "forward" direction, in the examples of FIG. 3B, from the top to the bottom of the regions surrounding the anatomic obstacle 362. The activation wave 372 conducts in a direction opposite to the normal direction, namely in a retrograde manner upward along the opposite side of the anatomic obstacle 362. The activation wave 372, if left uncorrected, will advance to the area upward along the right side and above the anatomic obstacle 362 and perpetuate an arrhythmia.

Thus, the circuit from 376→366→372 (i.e. clockwise) is defined as orthodromic, while the second wavefront 377 is antidromic, that is, in the opposite direction of the reentrant arrhythmia. An orthodromic and antidromic in this context refer to the direction of propagation of the reentrant arrhythmia around the obstacle. Collision of the orthodromic and antidromic activation wavefronts 372 and 377 can terminate the arrhythmia, but the presence of an excitable gap 378 allows the next cycle of orthodromic activation wave 376 to propagate the arrhythmia (as shown in 361). Collision of the antidromic activation wave 377 with the orthodromic activation wave 372 on the same cycle that the orthodromic activation wave 376 collides with refractory tail 368 (i.e. lack of excitable gap) extinguishes the arrhythmia (as shown in 363). As explained herein, NS and ATP therapies are utilized to terminate the activation wave 372. ATP therapy is used to extinguish a reentrant arrhythmia by causing simultaneous collision of the orthodromic cycle (376→366→372) ((n+1) with the refractory tail 368 of orthodromic cycle n), and the collision of antidromic activation wave 377 for cycle (n+1) with orthodromic activation wave 372 for cycle (n). NS therapy is used to modulate the EP substrate, at least one of the areas of slow conduction 364, the conduction velocity of the activation wavefronts, the refractory period (related to the length of refractory tail 368), and the extension of a functional obstacle 362.

A reentrant circuit 361 is shown to include delivery of an ATP therapy pacing pulse 374. The reentrant circuit 361 includes the activation wave 366, slow conduction zone 364, anatomic obstacle 362, and activation waves 370 and 372. The pacing pulse 374 is one of several pulses introduced within an ATP therapy. The pacing pulse 374 causes pacing waves 376 and 377 to begin propagating about both sides of the anatomic obstacle 362. The pacing wave 377 collides with the activation wave 372. The pacing wave 376 follows the refractory tail 368 through the excitable gap 378. While the example in the reentrant circuit 361 will entrain the activation wave 366, and the activation wave 372 collides with the head of the pacing wave 377, this does not terminate the arrhythmia. Instead, activation wave 370 continues to progress to excitable tissue advancing through the next arrhythmia cycle (N+1) and resets the tachycardia.

A reentrant circuit 363 is shown following application of an NS therapy, but during delivery of a pacing pulse 374 within an ATP pacing therapy. The reentrant circuit 363 includes the same activation wave 366 with activation waves 370 and 372, as well as the refractory tail 368. However, the refractory tail 368 in reentrant circuit 363 is significantly longer than the refractory tail 368 in the reentrant circuits 359 or 361. The refractory tail 368 is extended in response to delivery of certain types of NS therapy which result in prolongation of the refractory period of cardiac myocytes. Once the NS therapy is turned ON, this causes the cardiac myocytes to remain in a refractory state for a longer period of time. As the refractory tail 368 extends, the excitable gap 378 is reduced or becomes smaller. Hence, when the ATP therapy is delivered, pacing pulse 374 creates waves 376 and 377 that are more likely to collide with the refractory tail 368 and the activation wave 372 of the prior cycle. When the waves 376 and 377 for the n+1 collide with the head of the activation wave 372 for the cycle N, and collide with the refractory tail 368 for the same cycle N, this permits the ATP therapy to terminate the reentrant tachycardia. Hence, by making the excitable gap 378 shorter or smaller, the wave 376 is more likely to collide with the tail 368 of the reentrant activation and terminate the arrhythmia.

The NS therapy may be utilized to modulate EP substrate according to a pre-determined manner that was determined during mapping. The functional obstacle may be moved effectively bringing the reentrant circuit closer to the location of ATP stimulus.

A reentrant circuit 365 illustrates the situation in which the NS therapy is delivered in a manner configured to facilitate shifting the anatomical or functional obstacle 362 to a new position as denoted by position 380. The reentrant circuit 365 includes the activation wave 366 with activation waves 370 and 372, as well as the refractory tail 368. The NS therapy causes the reentrant circuit 365 to shift to position 380 which is further from a location at which the ATP therapy stimulus is delivered. Hence, when the ATP therapy is delivered, pacing pulse 374 causes waves 376 and 377 more likely to collide with the refractory tail 368 and the antidromic activation wave 372. When the waves 376 and 377 collide with the head of the activation wave 372 for the cycle N, and collide with the refractory tail 368 for the same cardiac N, this permits the ATP therapy to terminate the reentrant tachycardia. In physiologic terms the NS therapy may move the obstacle either closer or farther from the ATP site, depending on a number of factors specific to each scenario. Optionally, the shift in the position of the obstacle may result in not only a moved obstacle but an extended/enlarged obstacle as well. When the NS therapy causes the obstacle to enlarge or extend in length, the physical length of the reentrant circuit changes. Hence, the resultant reentrant circuit has a different cycle length due to the longer perimeter around which activation must propagate.

In accordance with one or more of the iterative methods described herein, when a first ATP therapy is unsuccessful to terminate an arrhythmia, NS therapy is enabled or modified. The new or modified NS configuration changes the combination of local conduction velocities and local refractory periods, and thereby "steers" the reentrant circuit 365 toward a select electrode side. For example, the reentrant circuit 365 may be steered toward the RA pacing lead or a CS pacing lead. For example, the NS therapy may be triggered to modulate EP substrate of the zone of functional block and adjacent areas. In this manner, the reentrant circuit 365 is moved anatomically closer to fixed-location electrodes on the permanently implanted cardiac leads, and therefore ATP is more likely to penetrate the circuit and achieve entrainment.

The NS therapy may be utilized to modulate EP substrate such that the zone of slow conduction in one branch of the reentrant circuit may be increased, thereby slowing the overall tachycardia cycle length. The next ATP stimulus collides with the refractory tail rather than advancing the tachycardia cycle. Optionally, the NS therapy may be used to increase or decrease the anatomic size of the slow-conducting zone of the reentrant circuit. This allows the paced wave front to penetrate more readily into the reentrant circuit, or makes it more likely for the paced wave front to collide with the refractory tail.

A reentrant circuit 367 illustrates the situation in which the NS therapy is delivered in a manner configured to facilitate lengthening of the slow conduction zone by a slow zone extension 381. The reentrant circuit 367 includes the activation wave 366, slow conduction zone 364, anatomic obstacle 362, and orthodromic and antidromic activation waves 370 and 372. The pacing pulse 374 causes pacing waves 376 and 377 to begin propagating about the anatomic obstacle 362 in both directions. The pacing wave 377 collides with the antidromic activation wave 372. The pacing wave 376 follows the refractory tail 368 through the excitable gap 378. By lengthening the slow conduction zone 364, 381, this slows the tachycardia cycle length. Hence, when the ATP therapy is delivered, pacing pulses 374 cause pacing waves 376 and 377 more likely to collide with the refractory tail 368 and the antidromic activation wave 372. When the pacing waves 376 and 377 collide with the head of the antidromic activation wave 372 for the cycle N, and collide with the refractory tail 368 for the same cardiac N, this permits the ATP therapy to terminate the reentrant tachycardia.

Alternatively, instead of increasing the refractory period, different protocols for NS therapies may be used instead to decrease the refractory period (e.g., the length of the refractory tail 368) by activating sympathetic neurons (e.g. through the use of higher amplitude NS pulses). By decreasing the refractory period, the excitable gap is made larger, thereby allowing the pacing waves 376 and 377 to penetrate further into the reentrant circuit 360 and promote entrainment that may be terminable by a premature extra stimulus.

As explained hereafter, NS therapies are turned on to decrease the complexity of a tachy-arrhythmia. For example, prolongation of the refractory periods, normalization of conduction velocities and reduced heterogeneity of refractoriness will promote a more organized reentrant arrhythmia. A more regular reentrant tachy-arrhythmia is more easily terminated by ATP therapies. The changes in the electrophysiology of the heart are believed to occur very soon after or nearly instantaneously with the delivery of the NS therapy, and thus after a few seconds (e.g. 5-10 seconds) following delivery of the NS therapy, the ATP therapy may be attempted. In the event that an ATP therapy does not terminate an arrhythmia, the NS therapy may be "dialed up", such as by progressively increasing the current amplitude of the NS pulses while monitoring characteristics of the tachycardia, such as the frequency/cycle length, organization or correlation of activation times at multiple sites, the local activation recovery interval, the post-pacing interval and the like. When sufficient changes occur in the monitored characteristics of the tachycardia, the next round of ATP therapy may be delivered at that time. Optionally, one or more NS electrodes may be provided, as an additional means of "step-wise" increases in the NS therapy output.

Figure 4A:
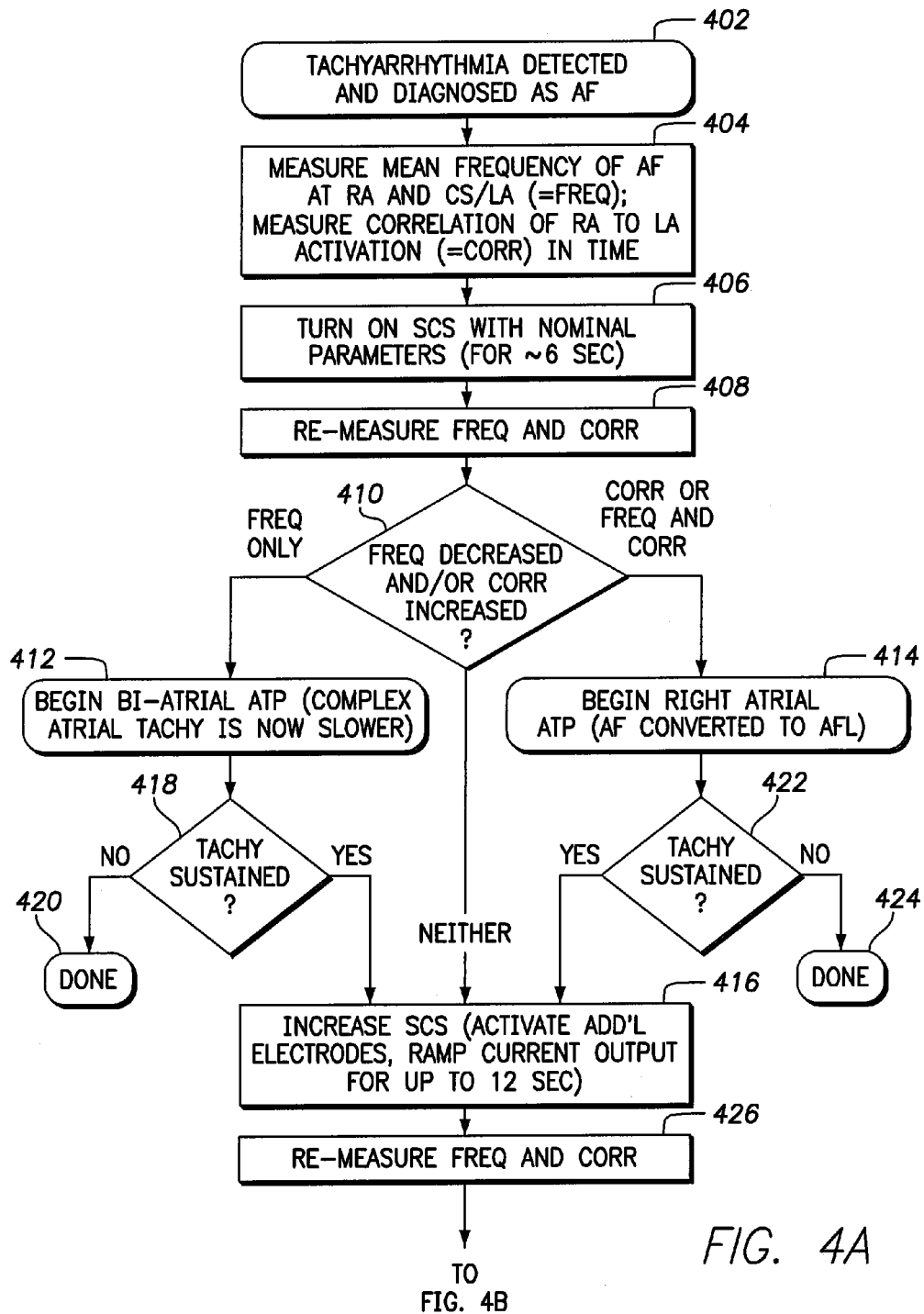
FIGS. 4A and 4B illustrate a processor implemented method performed by a system, device or other computer system to control NS assisted ATP therapy in accordance with an embodiment.
Figure 4B:
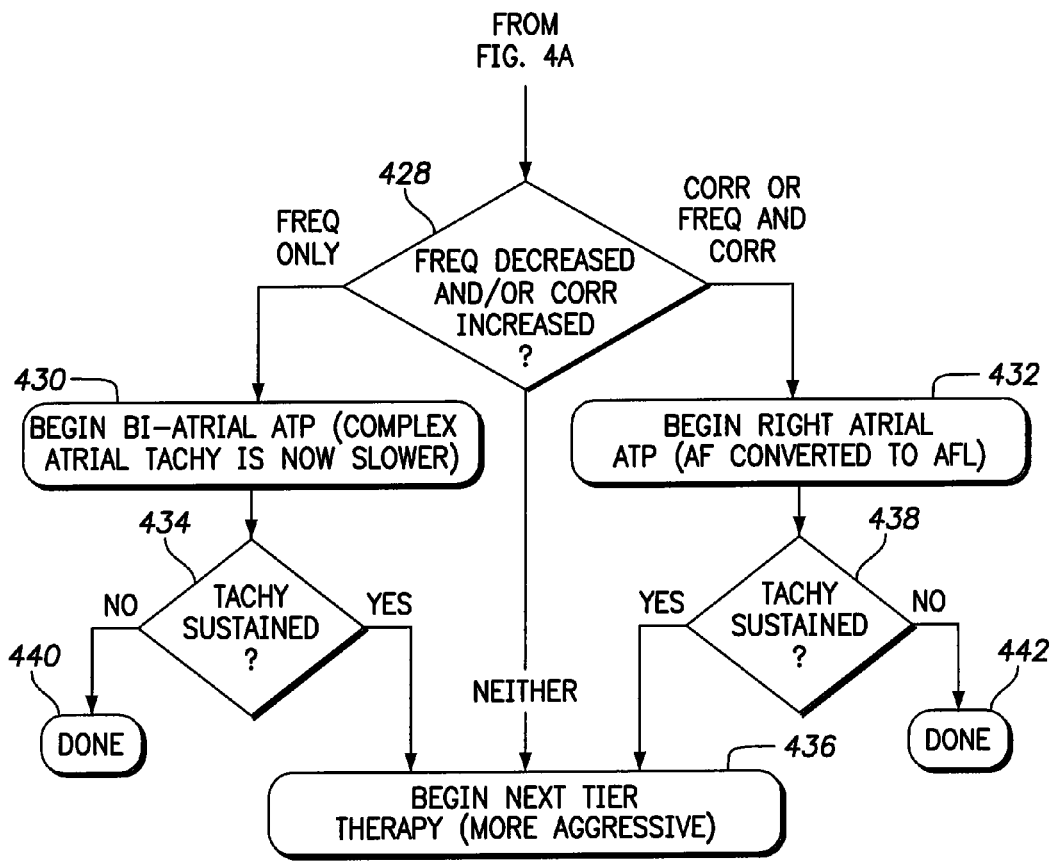

FIGS. 4A-4B illustrate a process implemented in accordance with an embodiment for coordinating delivery of NS and ATP therapies. Beginning at 402, the method detects the occurrence of a tachy-arrhythmia that is identified as atrial fibrillation (AF). The arrhythmia detection and identification of the type may be performed in accordance with various existing algorithms. The tachyarrhythmia may or may not be reentrant. In addition, the process of FIGS. 4A-4B may be used with focal tachyarrhythmias, as well, namely tachyarrhythmia that are driven by a focal trigger. The algorithm in FIGS. 4a-4B works irrespective of reentrant versus focal tachyarrhythmia; and further, even focal arrhythmias may sometimes be considered equivalent to micro reentrant arrhythmias according to some theories of arrhythmia mechanism.

At 404, the method measures select (pre-NS) characteristic values (CV), such as a mean frequency of the AF, as measured from the RA and/or as measured from the CS/LA, hereafter AF frequency. The method also measures, as a (pre-NS) CV, an amount of correlation between an activation time of the RA and an activation time of the LA, hereafter "RA-LA correlation". The AF frequency represents a rate-related physiologic characteristic, while the RA-LA correlation represents a stability-related physiologic characteristic. The AF frequency represents the rate of activation in the RA, such as the interval between successive atrial fibrillation activation events. The RA-LA correlation may be measured between one point in the RA and one or more points in the LA. For example, when multiple LA electrodes are provided at different sites about the LA, one or more of these different sites may be used to sense for LA activity. The activation time may represent an initial point in time at which electrical activity is sensed at a corresponding site. For example, the RA activation time may be the point in time at which the electrical activity above a minimum threshold is sense at an RA electrode. Alternatively, the activation time may be determined based on sensed electrical activity over a period of time, a "center of mass" or average for electrical activity sensed over Xmsec. The activation time may be based on various activation events within the corresponding cardiac cycle. For example, the activation event may be associated with the occurrence of a P-wave in an IEGM.

At 406, the method delivers an initial NS therapy utilizing a first NS operating configuration. At 408, the AF frequency and RA-LA correlation are re-measured to collect a new AF frequency and a new RA-LA correlation. Before and after delivering of the NS therapy, the method measures characteristic values for a rate-related physiologic characteristic (rate RPC) and for a stability-related physiologic characteristic (stability RPC). The rate RPC is indicative of a frequency of an reentrant circuit within the tachyarrhythmia. The stability RPC is indicative of a spatio-temporal stability of the arrhythmia.

At 410, the method analyzes the characteristic values for the rate and stability RPCs for differences, between the rate and stability RPCs, pre-NS and post-NS therapy to determine a rate RPC difference and a stability RPC difference. For example, the new and prior AF frequencies are compared and new and prior RA-LA correlations are compared. The comparisons of AF frequencies and RA-LA correlations derive rate and stability RPC difference information regarding a reentrant circuit. For example, when the new RA-LA correlation increases relative to the prior RA-LA correlation, this is a stability RPC difference that is an indication that an atrial tachy-arrhythmia has become less complex. When the new RA-LA correlation remains the same as or decreases relative to the prior RA-LA correlation, this is a stability RPC difference indicating that the atrial tachy-arrhythmia is remaining at a current level of complexity or is becoming more complex. When the difference between the new and prior AF frequencies is negative (i.e. new frequency is lower than the prior frequency), this is a rate RPC difference indication that an atrial tachy-arrhythmia is slowing. When the difference between the new and prior AF frequencies is positive (i.e. new frequency is higher than the prior frequency), this is an indication that an atrial tachy-arrhythmia is speeding up. When an atrial tachy-arrhythmia maintains an initial level or increases complexity, it is desirable to deliver a bi-atrial ATP therapy. However, when an atrial tachy-arrhythmia reduces in complexity, regardless of whether the AF frequency decreases, this may be an indication that the arrhythmia has converted from atrial fibrillation (AF) to atrial flutter (AFL).

Hence, at 410, when the CV analysis determines that the AF frequency decreases but the RA-LA correlation does not increase, flow moves to 412. At 412, bi-atrial ATP therapy is delivered. At 410, when the CV analysis determines that the RA-LA correlation increases (regardless of whether AF frequency decreases), flow moves to 414. At 414, mono-atrial (typically right atrial) ATP therapy is delivered. The term "mono-atrial" is used to mean that the ATP therapy is delivered only to a single atrium and not to the other atrium. If the CV analysis determines that the RA-LA correlation does not increase and the AF frequency does not decrease, then flow moves to 416. Hence, the method delivers different ATP therapies based on the type associated with the tachyarrhythmia, the rate RPC difference and the stability RPC difference.

After the ATP therapy is delivered at 412, flow moves to 418, where the method determines whether the tachy-arrhythmia is sustained or has been terminated. If the tachy-arrhythmia is terminated, flow moves to 420 and the process is done. Alternatively, if the tachy-arrhythmia is not terminated, flow moves to 416.

Similarly, after the ATP therapy is delivered at 414, flow moves to 422, where the method determines whether the tachy-arrhythmia is sustained or has been terminated. If the tachy-arrhythmia is terminated, flow moves to 424 and the process is done. Alternatively, if the tachy-arrhythmia is not terminated, flow moves to 416.

At 416, the NS therapy is changed by increasing one or more NS therapy configuration parameters. For example, the configuration parameters to adjust may include one or more stimulus phase, frequency, pulse width, pulse amplitude, number of active electrodes, active electrode pattern, active electrode position within electrode array, active electrode placement with respect to a reference anatomy. The change may increase one or more of the configuration parameters. Once the configuration parameters for the NS therapy are changed, the new NS therapy is delivered at 416.

At 426, the AF frequency and the RA-LA correlation are re-measured. At 428, the new and prior AF frequencies are compared and new and prior RA-LA correlations are compared to obtain rate and stability RPC differences pre-NS and post-NS therapy.

When flow moves through 412 to 418 to 416 and to 426, or moves through 414 to 422 to 416 to 426, then the AF frequency and RA-LA correlation measured at 426 represent "updated" characteristic values that are measured after delivery of the post-ATP increased NS therapy, namely after ATP and after delivery of an increased NS therapy. The increased NS therapy represents a second or subsequent NS therapy after a first or prior NS therapy. Similarly, the analysis at 428 represents an analysis of updated CVs for rate and stability RPC differences between pre-ATP and first NS therapies CVs and post-ATP and increased NS therapies CVs.

Similar to the comparison at 410, at 428, when the AF frequency decreases but the RA-LA correlation does not increase, flow moves to 430. At 430, bi-atrial ATP therapy is delivered. At 428, when the RA-LA correlation increases (regardless of whether AF frequency decreases), flow moves to 432. At 432, right atrial ATP therapy is delivered. If the RA-LA correlation does not increase and the AF frequency does not decrease, then flow moves to 436.

After delivering the corresponding ATP therapies at 430 or 432, flow moves to 434 or 438, respectively. At 434 and 438, it is determined whether the tachy-arrhythmia has been terminated or sustained. When the tachy-arrhythmia is terminated, flow moves from 434 to 440 or from 438 to 442. When the tachy-arrhythmia is not terminated, flow moves to 436. At 436, the process moves to a more aggressive, or next tier, of ATP therapy and/or atrial cardioversion therapy and/or NS therapy.

In accordance with the foregoing method, the NS therapy and ATP therapy are modified based upon the results of the NS therapy and the effect of the NS therapy on the electric physiology substrate.

Figure 5A:
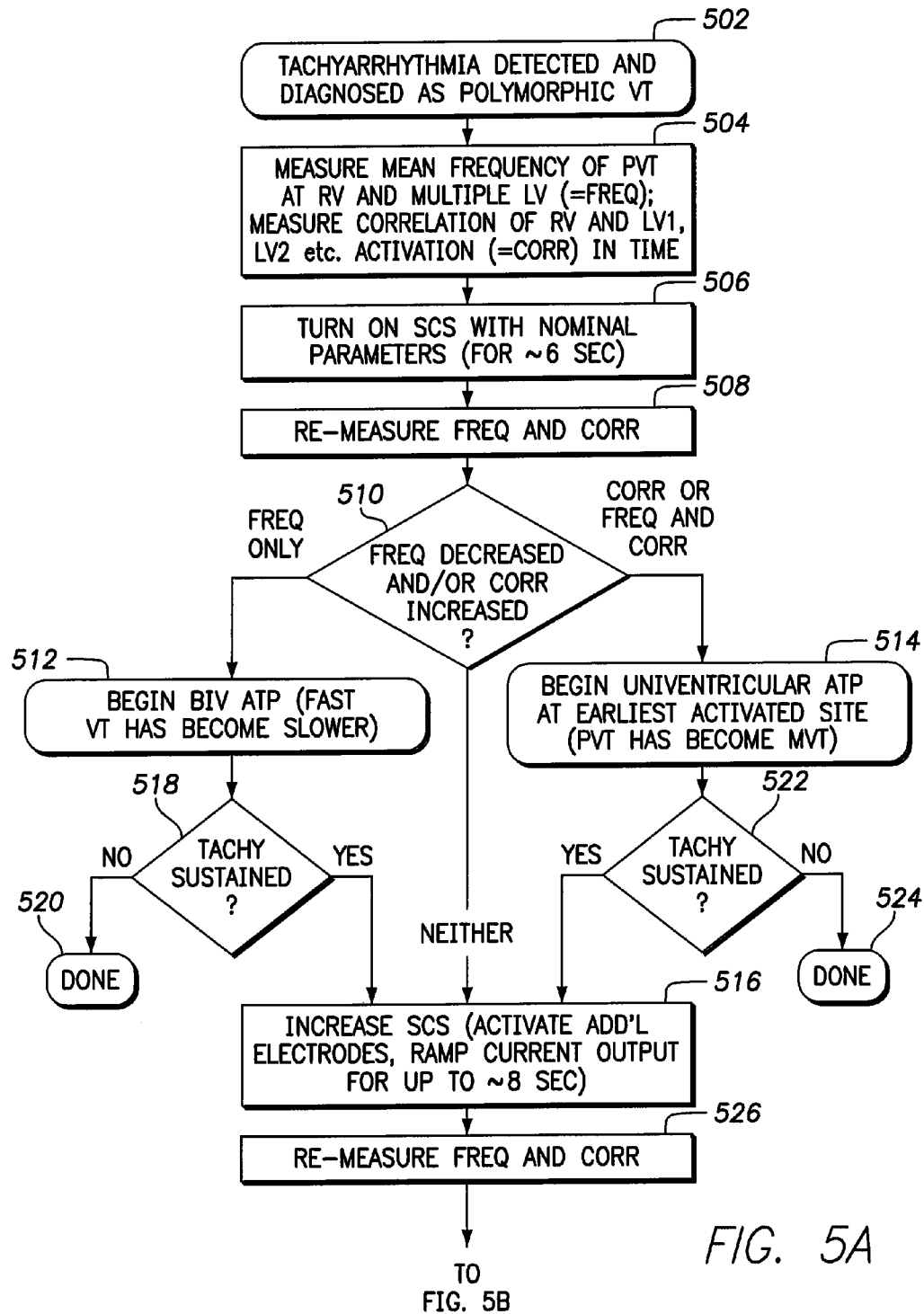
FIGS. 5A and 5B illustrate a computer implemented method performed by one or more of the devices and systems described herein, to control NS assisted ATP therapy in accordance with an embodiment.
Figure 5B:
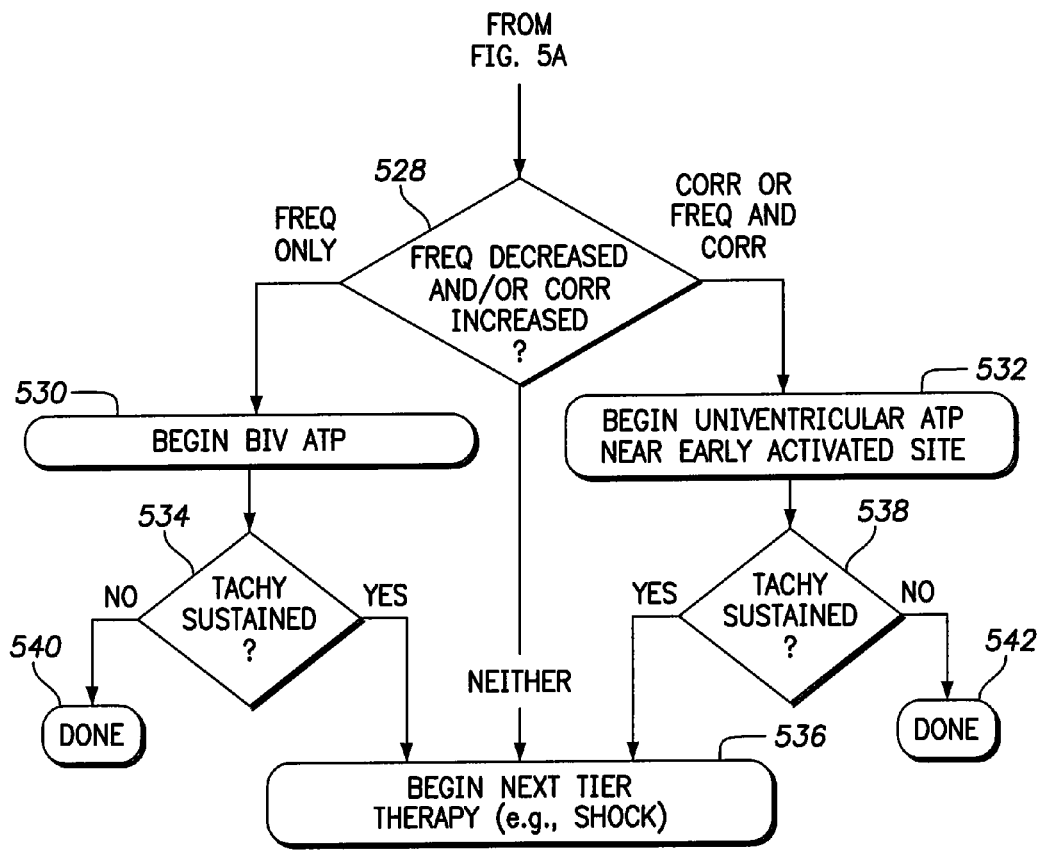

FIGS. 5A-5B illustrate a process implemented in accordance with an embodiment for coordinating delivery of NS and ATP therapies when polymorphic VT is diagnosed. Beginning at 502, the method detects the occurrence of a tachy-arrhythmia and identifies or diagnoses the tachy-arrhythmia type to be polymorphic ventricular tachycardia (VT). The arrhythmia detection and identification may be performed in accordance with various existing algorithms. The algorithm in FIGS. 5A-5B works irrespective of reentrant versus focal tachyarrhythmia (e.g. driven by a focal trigger). Further, even focal arrhythmias may sometimes be considered equivalent to microreentrant arrhythmias according to some theories of arrhythmia mechanism.

At 504, the method measures a pre-NS therapy CV, such as mean frequency of the VT, as measured from the RV and/or as measured from the LV, hereafter VT frequency. The method also measures, as another pre-NS therapy CV, an amount of correlation between an activation time of the RV and an activation time of the LV, hereafter "RV-LV correlation". The VT frequency and RV-LV correlation represent rate and stability RPCs, and are "pre-NS therapy". The VT frequency represents the rate of activation in the RV, such as the interval between successive ventricular activation events. The RV-LV correlation may be measured between one or more points in the RV and one or more points in the LV. For example, when multiple LV electrodes may be provided at different sites about the LV, one or more of these different sites may be used to sense for LV activity. The activation time may represent an initial point in time at which electrical activity is sensed at a corresponding site. For example, the RV activation time may be the point in time at which the electrical activity above a minimum threshold is sense at an RV electrode. Alternatively, the activation time may be determined based on sensed electrical activity over a period of time, a "center of mass" or average for electrical activity sensed over Xmsec. The activation time may be based on various activation events within the corresponding cardiac cycle. For example, the activation event may be associated with the occurrence of a T-wave in an IEGM.

At 506, the method delivers an initial NS therapy utilizing a NS operating configuration. At 508, the VT frequency and RV-LV correlation are re-measured to collect post-NS therapy rate and stability RPCs.

At 510, the new (post-NS therapy) and prior (pre-NS therapy) VT frequencies are compared and new and prior RV-LV correlations are compared. The comparisons of VT frequencies and RV-LV correlations derive rate and stability RPC difference information regarding a tachyarrhythmia. For example, when the new RV-LV correlation increases relative to the prior RV-LV correlation, this is a stability RPC difference indicating that a ventricular tachy-arrhythmia has become less complex. When the new RV-LV correlation remains the same as or decreases relative to the prior RV-LV correlation, this is a stability RPC difference indicating that the ventricular tachy-arrhythmia is remaining at a current level of complexity or is becoming more complex. When the rate RPC difference between the new and prior VT frequencies is negative (i.e. new rate RPC is lower than prior rate RPC), this an indication that a ventricular tachy-arrhythmia is slowing. When the rate RPC difference between the new and prior VT frequencies is positive (i.e. new rate RPC is higher than prior rate RPC), this is an indication that a ventricular tachy-arrhythmia is speeding up. When a ventricular tachy-arrhythmia maintains an initial level of complexity following NS therapy, it is desirable to deliver a bi-ventricular ATP therapy. However, when a ventricular tachy-arrhythmia reduces in complexity following NS therapy, regardless of whether the VT frequency decreases, this may be an indication that the arrhythmia has converted from polymorphic VT to monomorphic VT and may thus amenable to termination by uni-ventricular ATP.

Hence, at 510, when the analysis of the rate and stability RPC differences indicates that the VT frequency decreases, but the RV-LV correlation does not increase, flow moves to 512. At 512, bi-ventricular ATP therapy is delivered. At 510, when the RV-LV correlation increases (regardless of whether VT frequency decreases), flow moves to 514. At 514, right uni-ventricular ATP therapy is delivered near the earliest activation site. The earliest activation site may be determined based on the first electrode in the RV or LV to sense activity associated with a current cardiac cycle. At 510, if the RV-LV correlation does not increase and the VT frequency does not decrease, then flow moves to 516.

After the ATP therapy is delivered at 512, flow moves to 518, where the method determines whether the tachy-arrhythmia is sustained or has been terminated. If the tachy-arrhythmia is terminated, flow moves to 520 and the process is done. Alternatively, if the tachy-arrhythmia is not terminated, flow moves to 516.

Similarly, after the ATP therapy is delivered at 514, flow moves to 522, where the method determines whether the tachy-arrhythmia is sustained or has been terminated. If the tachy-arrhythmia is terminated, flow moves to 524 and the process is done. Alternatively, if the tachy-arrhythmia is not terminated, flow moves to 516.

At 516, the NS therapy is changed by increasing one or more parameters associated with the NS operating configuration. The change may increase one or more of the configuration parameters. Once the configuration parameters for the NS therapy are changed, the new NS therapy is delivered at 516. At 526, the VT frequency and the RV-LV correlation are re-measured. At 528, the new and prior VT frequencies are compared and new and prior RV-LV correlations are compared. When the analysis at 528 follows ATP therapy at 512 or 514, the comparison/analysis is between pre-ATP (corresponding to the first NS) and post-ATP (corresponding to the increased NS) (updated) characteristic values associated with rate RPC and stability RPC, to determine a post-ATP/increased NS rate RPC difference and a post-ATP/NS stability RPC difference.

Similar to the comparison discussed above at 510, at 528, when the VT frequency decreases but the RV-LV correlation does not increase, flow moves to 530. At 530, bi-ventricular ATP therapy is delivered. At 528, when the RV-LV correlation increases (regardless of whether VT frequency decreases), flow moves to 532. At 532, right uni-ventricular ATP therapy is delivered near the earliest activation site. If the RV-LV correlation does not increase and the VT frequency does not decrease, then flow moves to 536.

After delivering the corresponding NS therapies at 530 or 532, flow moves to 534 or 538, respectively. At 534 and 538, it is determined whether the tachy-arrhythmia has been terminated or sustained. When the tachy-arrhythmia is terminated, flow moves from 534 to 540 or from 538 to 542. When the tachy-arrhythmia is not terminated, flow moves to 536. At 536, the process moves to a more aggressive or next tier of, ATP therapy and/or NS therapy.

In accordance with the foregoing method, the NS therapy and ATP therapy are configured to respond to polymorphic VT and are modified based upon the results of the NS therapy and the effect of the NS therapy on the state of the reentrant circuit(s) causing the polymorphic VT.

Figure 6:
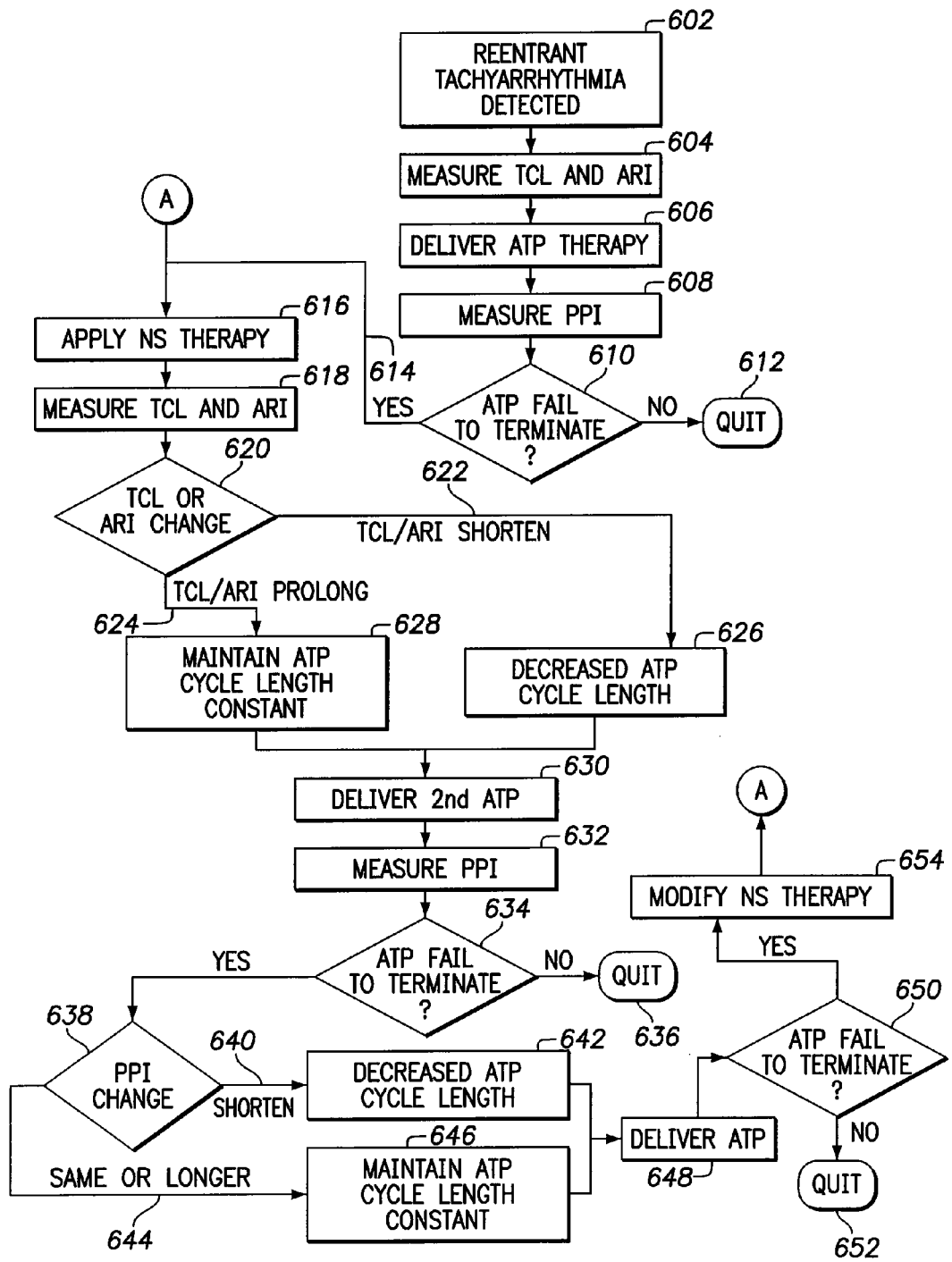
FIG. 6 illustrates a computer implemented method performed by one or more of the devices and systems described herein, to control NS assisted ATP therapy in accordance with an embodiment.

FIG. 6 illustrates a process implemented in accordance with an embodiment for coordinating delivery of NS and ATP therapies. Beginning at 602, the method detects the occurrence of a reentrant tachy-arrhythmia. The arrhythmia detection may be performed in accordance with various existing algorithms. The Post-Pacing Interval measurement relies on entrainment of the reentrant arrhythmia and assessing the "echo time." The methods of FIGS. 4A-4B and 5A-5B would apply equally well to focal or reentrant tachyarrhythmias.

At 604, the method measures a tachycardia cycle length (TCL) and a local activation recovery interval (ARI) as CVs. The TCL represents a rate RPC, namely the rate of activation to activation, such as the interval between successive atrial activation events. Alternatively, the rate of activation may be based on the interval between successive ventricular activation events and the like. The TCL is determined by identifying common activation points in successive cardiac cycles for a chamber of interest, such as the atrium or ventricle. The ARI represents a stability RPC, namely the time between an activation event and an end-of-repolarization within the corresponding cardiac cycle. For example, the end-of-repolarization may be associated with the occurrence of a T-wave in an IEGM. Alternatively, the end-of-repolarization may be determined based on a predetermined low frequency repolarization wave that is measured in an atrium such as a T-wave. Hence, when the end-of-repolarization is measured from the T-wave in the ventricle, as one example, the ARI interval may be the interval between the occurrence of a ventricular event and the next successive T-wave. When the end-of-repolarization is measure from the T-wave in the atrium, as another example, the ARI interval may be the interval between the occurrence of an atrial event and the next successive T-wave.

Optionally, a peak of the local repolarization wave (i.e. in a chamber of interest) may be used as a surrogate for the end-of-repolarization given that the peak of a local repolarization wave is relatively easy to measure.

At 606, the method delivers an initial ATP therapy utilizing an NS operating configuration associated with the type of tachy-arrhythmia. At 608, a post-pacing interval (PPI) is measured. The PPI represents the time between the last delivered ATP stimulus and a subsequent local next event detected at the same electrode from which the ATP stimulus was delivered. For example, when an ATP stimulus is delivered from an electrode in the right atrium, the PPI is determined as the time between the last delivered atrial ATP stimulus and the next subsequent local event detected at the same atrial electrode. The length of the PPI and the TCL can be compared to derive certain information regarding a distance between a pacing/sensing electrode and a reentrant circuit within the chamber of the pacing/sensing electrode. For example, when the PPI is longer than the TCL, the amount of time that the PPI is longer than the TCL relates to the amount of distance between the pacing/sensing electrode and the reentrant circuit. As this distance between the pacing/sensing electrode and reentrant circuit shortens, the difference in length between the PPI and TCL similarly shortens. In the extreme case where PPI equals TCL, the pacing location is within the reentrant circuit. As explained hereafter, changes in the TCL and PPI are used at different stages in the present method to determine whether to modify the NS and/or ATP therapy.

Returning to FIG. 6, at 610, the method determines whether the ATP therapy has failed to terminate the arrhythmia. If the ATP therapy is successful (i.e. terminates the tachy-arrhythmia), the process quits at 612. Alternatively, when the ATP therapy fails to terminate the tachy-arrhythmia, flow advances along 614. At 616, the method applies a new NS therapy. At 618, the TCL and ARI are re-measured. At 620, the new (post-NS) and old (pre-NS) TCL are compared and the new (post-NS) and old (pre-NS) ARI are compared to determine whether changes have occurred. At 620, the CVs are analyzed for rate and stability RPC differences. When a change occurs in one or both of the TCL and/or ARI difference, flow advances along one of paths 622 and 624 depending upon the direction of change in the TCL and/or ARI. More specifically, when the TCL shortens or the ARI shortens, or both, flow moves along 622 to 626. At 626, the ATP cycle length is decreased such that a different ATP therapy is defined for delivery. Returning to 620, when the TCL lengthens or is prolonged, and/or the ARI lengthens or is prolonged, flow moves along 624 to 628. At 628, the method maintains the prior ATP cycle length at a constant level to be delivered during the next ATP therapy. Returning to 620 again, optionally further comparisons between the TCL and ARI may be made. For example, if the TCL shortens, but the ARI is prolonged, a priority may be defined such that one of the TCL and ARI take priority. For example, when the TCL is afforded priority, flow will branch along 622 and 624 based on the TCL first, regardless of whether the ARI changes or in which direction the ARI changes. If the TCL maintains a constant length or remains within a predetermined range of its initial measurement, then the determination at 620 may be based on the ARI. Alternatively, the ARI may be afforded priority at 620 such that flow branches between 622 and 624 based first on the ARI, regardless of change in the TCL.

As a further option, each of or both of the TCL and ARI may be afforded ranges around the initial measurements of 604, such that the branch at 620 only occurs when one or both of the TCL and ARI shorten or are prolonged beyond this predetermined range surrounding the original TCL and ARI measurements.

Continuing with the process of FIG. 6, once the ATP cycle length has been decreased or maintained constant, flow moves to 630 where a second ATP therapy is delivered with the new cycle length. Next at 632, the PPI is re-measured. At 634, the method determines whether the ATP therapy failed to terminate. When the ATP therapy is successful and terminates the tachy-arrhythmia, flow moves to 636 where the method quits. Alternatively, when the ATP therapy fails to terminate the arrhythmia, flow moves to 638. At 638, the method determines whether the PPI has changed between the measurements at 608 and 632. When the change in the PPI indicates that the new PPI is shorter, flow moves along 640 to 642 where the ATP cycle length is decreased. At 638, when the PPI is determined to be the same or longer at the measurement taken at 632 when compared to the measurement at 608, flow moves along 644 to 646 where the ATP cycle length is maintained constant. Once the ATP cycle length has either been maintained constant or decreased, flow moves to 648 where the next ATP therapy is delivered. Next, at 650 the method determines whether the ATP therapy failed to terminate the tachy-arrhythmia. If the tachy-arrhythmia is terminated, the process quits at 652. Otherwise, flow moves to 654 where the NS therapy is modified. Once the NS therapy is modified at 654, flow moves along branch A back 616 where the NS therapy is applied. Thereafter, the process continues between 616 and 654 again.

In accordance with the foregoing process, NS therapies are applied to modulate tissue and nerves of interest until an arrhythmia terminates.

When the TCL changes, this is an indication that the preceding NS therapy has modified the conduction velocity or has modified the path length of the reentrant circuit. As one example when the TCL shortens, this is an indication that the conduction velocity is now faster or the reentrant core has become smaller. Alternatively, when the TCL becomes prolonged, this is an indication that the conduction velocity has become slower or that the reentrant core has grown larger. If the conduction velocity has increased or an obstacle has been modified such that the path length becomes shorter, then decreasing the ATP cycle length for the next ATP therapy is desirable. Alternatively, when the conduction velocity becomes slower or the obstacle modification causes the path length to grow longer, then it is desirable to maintain the ATP cycle length the same or lengthen the ATP cycle length for the next ATP therapy.

When the ARI changes at the pacing/sensing electrode, this in interpreted as an indication that the NS therapy has modified the re-polarization/refractoriness of tissue. The prolongation of refractoriness at a pacing/sensing electrode represents a reasonable surrogate for prolongation of refractoriness near a reentrant circuit associated with an arrhythmia. Hence, when the ARI increases, the above method maintains the ATP cycle length for the next ATP cycle therapy at the same cycle length as prior ATP therapy. Alternatively, when the ARI decreases, the method decreases the ATP cycle length for the next ATP therapy relative to the prior ATP therapy.

Optionally, at 642 the ATP cycle length may be decreased in an amount based upon and relative to the TCL measured at 618. For example, the ATP cycle length set at 642 may be set to be slightly faster than the second TCL measured at 618.

When the PPI from the second ATP therapy is the same or equal, or longer than the PPI measured following the delivery of the first therapy (at 606), the method may set the next ATP cycle length to be faster than the current ATP cycle length at 646.

In accordance with the foregoing method, the NS therapy and ATP therapy are modified based upon the results of the NS therapy and the effect of the NS therapy on the electric physiology substrate.

Figure 7:
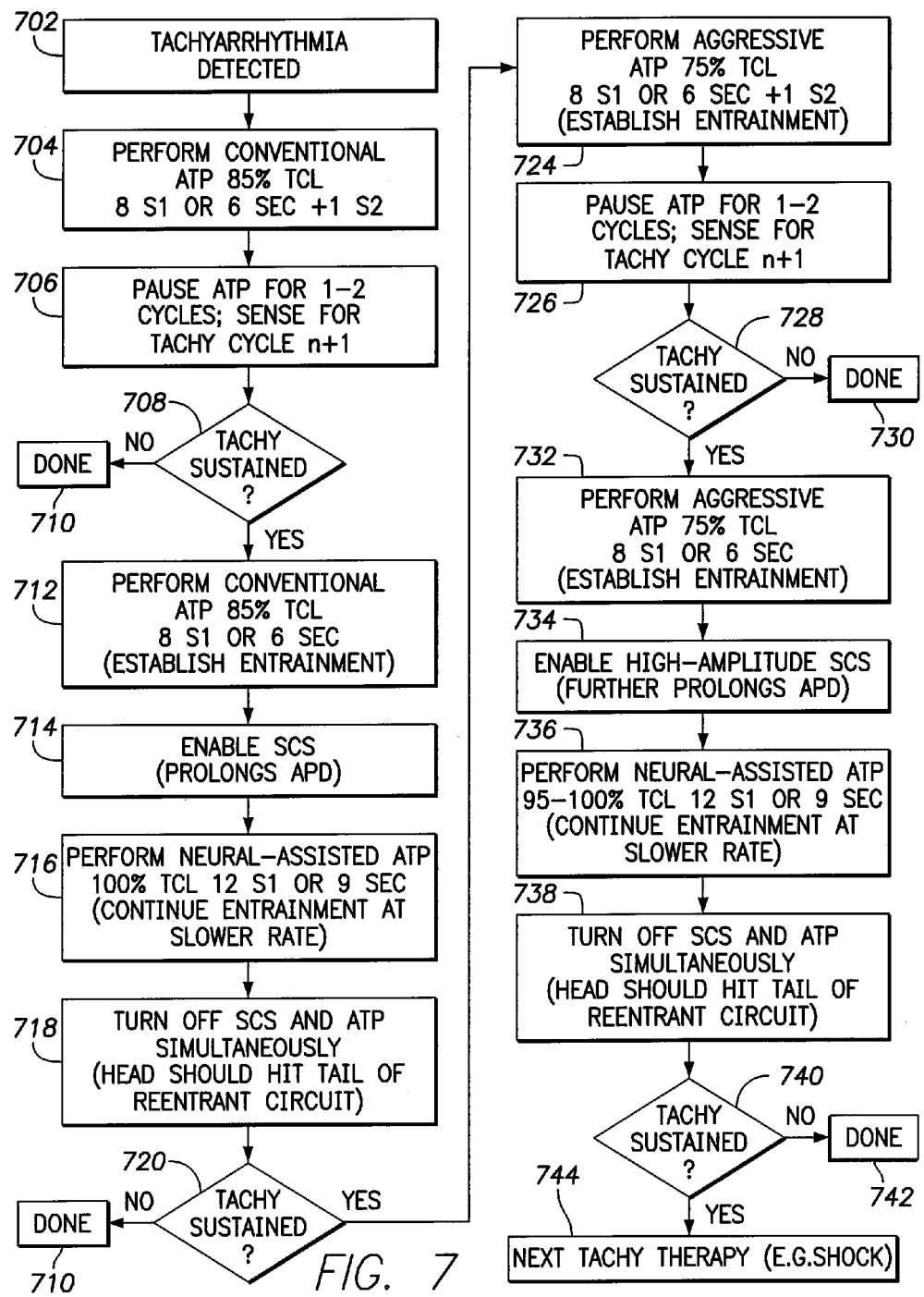
FIG. 7 illustrates a process implemented in accordance with an embodiment for coordinating delivery of NS and ATP therapies.

FIG. 7 illustrates a process implemented in accordance with an embodiment for coordinating delivery of NS and ATP therapies. Beginning at 702, the method detects the occurrence of a reentrant tachy-arrhythmia. Upon tachycardia detection, at 704 an ATP therapy is performed, for example with a train of 8 stimuli (S1) at slightly faster than the tachycardia cycle length (TCL) (e.g., 85% of the TCL). Optionally, the ATP therapy may include more or fewer stimuli pulses. If the programmed stimulation (train of stimuli) penetrates the reentrant circuit, entrainment will result and the tachy activation will follow 1:1 by the end of the pulse train, at 85% of the original TCL. Hence, a single premature extra-stimulus (S2), following the train of S1 stimuli, may be delivered (20-300 ms shorter than the S1 cycle length delivered immediately following the last S1 pulse). The extra-stimulus may terminate the tachycardia by colliding with the tail of refractory tissue and the head of the oncoming activation.

At 706, the method pauses the ATP therapy for a predetermined number of cardiac cycles and senses for a tachycardia during the N+1 cardiac cycle. At 708, the method determines whether the tachycardia is sustained or terminated. If the extra stimulus S2 terminates the tachycardia, nothing more is needed and the method stops at 710. Otherwise flow moves to 712.

When the extra stimulus S2 does not terminate the tachycardia, the extra-stimulus S2 may instead only reset and advance the tachycardia. When the tachycardia is advanced by the extra stimulus S2, the next sensed activation comes at the interval between S1 and S2 which is shorter than the interval between successive ATP pulse trains (the S1-S1 interval). Hence, at 708, the method will sense activation having a TCL corresponding to the S1-S2 interval. If this happens, further decreasing the S1-S2 interval poses a risk to accelerate the tachycardia instead of terminating it.

Therefore, for the next ATP delivery, at 712, the arrhythmia is first entrained by an ATP pulse train S1 (e.g., 6 seconds, or 8 S1 pulses set at 85% of the TCL). Next, at 714, instead of a premature extra-stimulus S2, an NS therapy is turned on. At 716, the cycle length of the S1 pulse train is increased to 100% of the TCL. The NS therapy is turned on to prolong the refractory period and the S1 interval is slowed to 100% of the TCL in order to maintain entrainment. The NS therapy and the ATP pulse train S1 are delivered for several cardiac cycles while entrainment is maintained, referred to as entrained cycles (for example 12 S1 pulse trains or a pulse train delivered for approximately 9 seconds).

Thereafter, at 718, the NS therapy and the ATP therapy are simultaneously turned off. The NS therapy may take a few seconds for the effects of the NS therapy to wash out. Hence, the head of the N+1 reentrant cycle should meet the tail of the N reentrant cycle, thereby terminating the arrhythmia.

At 720, the method determines whether the arrhythmia persists. If not, the method is done at 722. If the arrhythmia still fails to terminate, a more aggressive set of programmed stimulation pulses S1 and single premature extra stimulus S2 are delivered. For example, at 724, a pulse train of 8 S1 pulses or 6 seconds of S1 pulses are delivered at a rate of 75% of the TCL followed by an extra stimulus pulse S2. At 726, the ATP therapy is paused for 1-2 cycles and the method senses for the tachy arrhythmia during cycle N+1. At 728, if the tachy arrhythmia is not sustained/maintained, the method is done at 730. Otherwise, the method continues to 732.

At 732, a more aggressive ATP therapy is delivered. At 734, a high amplitude NS therapy is delivered. At 736, the ATP therapy is changed to 95-100% TCL in conjunction with a higher dose of NS therapy to further prolong refractoriness. At 738, when both the NS therapy and the ATP therapy are quickly removed, there is a high likelihood of head-meets-tail termination of the reentrant activation. Alternatively, a gradual change or a series of discrete steps can be made in both NS therapy and ATP therapy to maintain entrainment; in the preferred case, the rate of change of NS and ATP rate are slightly different in order to promote the possibility of the reentrant wave front colliding with itself (head-meets-tail) or with the n+1 entrainment pulse. At 740, in case this still fails, flow moves to 744 where the next tier of therapy (for example DC shock) is administered. Otherwise, the method is done at 742.

It is to be understood that the above description is intended to be illustrative and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method to provide a neural stimulation (NS) therapy to assist anti-tachycardia pacing (ATP) therapy, the method comprising:
   detecting a tachyarrhythmia and identifying a type associated with the tachyarrhythmia;
   delivering an NS therapy utilizing a first NS operating configuration;
   before and after delivery of the NS therapy, measuring characteristic values for a rate-related physiologic characteristic (rate RPC) and for a stability-related physiologic characteristic (stability RPC), the rate RPC indicative of a frequency of at least one of an reentrant circuit and a focal trigger driving the tachyarrhythmia, the stability RPC indicative at least one of a spatio-temporal stability of the arrhythmia and underlying electrical substrate,
   analyzing the characteristic values for the rate and stability RPCs for differences, between the rate and stability RPCs, pre-NS and post-NS therapy to determine a rate RPC difference and a stability RPC difference; and
   delivering different ATP therapies based on the type associated with the tachyarrhythmia, the rate RPC difference and the stability RPC difference.

2. The method of claim 1, wherein the rate RPC represents a frequency of atrial fibrillation (AF) and the stability RPC represents correlation of right atrial (RA) to left atrial (LA) activation time over multiple cardiac cycles.

3. The method of claim 1, wherein the rate RPC represents a frequency of polymorphic ventricular tachycardia (poly VT), and the stability RPC represents correlation of right ventricular (RV) to left ventricular (LV) activation time over multiple cardiac cycles.

4. The method of claim 1, wherein the rate RPC represents a tachycardia cycle length (TCL) and the stability RPC represents at least one of a spatial dispersion of an activation recovery interval (ARI), and a temporal dispersion of the ARI.

5. The method of claim 2, wherein the delivering of ATP therapy includes delivering only mono-atrial ATP to a single one of an RA and an LA when the correlation of the RA to LA activation increases.

6. The method of claim 2, wherein the delivering of ATP therapy represents delivering bi-atrial ATP when the frequency of AF decreases and the correlation of the RA to LA activation does not increase.

7. The method of claim 2, further comprising increasing the NS therapy when the frequency of AF does not decrease and the correlation of the RA to LA activation does not increase.

8. The method of claim 3, further comprising increasing the NS therapy when the frequency of VT does not decrease and the correlation of the RV to LV activation does not increase.

9. The method of claim 1, further comprising:
   after delivering of the ATP therapy, measuring post-ATP characteristic values for the rate and stability RPCs;
   analyzing the post-ATP characteristic values for the rate and stability RPCs for differences, pre-ATP and post-ATP therapy to determine a post-ATP rate RPC difference and a post-ATP stability RPC difference; and
   delivering at least one of a different ATP therapy and a different NS therapy based on the differences in the post-ATP rate RPC difference and the post-ATP stability RPC difference.

10. The method of claim 9, wherein the post-ATP rate RPC represents a frequency of atrial fibrillation (AF) and the post-ATP stability RPC represents correlation of RA to LA activation in time.

11. The method of claim 10, wherein the delivering of ATP therapy includes delivering only mono-atrial ATP when the correlation of the RA to LA activation increases.

12. The method of claim 10, wherein the delivering of ATP therapy represents delivering bi-atrial ATP when the frequency of AF decreases and the correlation of the RA to LA activation does not increase.

13. The method of claim 10, further comprising increasing the NS therapy when the frequency of AF does not decrease and the correlation of the RA to LA activation does not increase.

14. The method of claim 1, further comprising turning ON the NS therapy, when the type of the tachyarrhythmia detected represents a hemodynamically unstable arrhythmia, to slow a tachycardia cycle length and convert the tachyarrhythmia to a hemodynamically stable arrhythmia.

15. A system to provide a neural stimulation (NS) therapy to assist anti-tachycardia pacing (ATP) therapy, the system comprising:
   an arrhythmia detection module configured to detect a tachyarrhythmia and identify a type associated with the tachyarrhythmia;
   an NS module configured to deliver an NS therapy utilizing at least a first NS operating configuration;
   a measurement module configured to measure, before and after delivering of the NS therapy, characteristic values for a rate-related physiologic characteristic (rate RPC) and for a stability-related physiologic characteristic (stability RPC), the rate RPC indicative of a frequency of at least one of an reentrant circuit and a focal trigger driving the tachyarrhythmia, the stability RPC indicative of a spatio-temporal stability of the arrhythmia and/or underlying electrical substrate,
   an analysis module configured to analyze the characteristic values for the rate and stability RPCs for differences, between the rate and stability RPCs, pre-NS and post-NS therapy to determine a rate RPC difference and a stability RPC difference; and
   an ATP module configured to deliver different ATP therapies based on the type associated with the tachyarrhythmia, the rate RPC difference and the stability RPC difference.

16. The system of claim 15, wherein the rate RPC represents a frequency of atrial fibrillation (AF) and the stability RPC represents correlation of RA to LA activation time over multiple cardiac cycles.

17. The system of claim 15, wherein the rate RPC represents a frequency of polymorphic ventricular tachycardia (poly VT), and the stability RPC represents correlation of RV and LV activation time over multiple cardiac cycles.

18. The system of claim 15, wherein the rate RPC represents a tachycardia cycle length (TCL) and the stability RPC represents spatial dispersion of local activation recovery interval (ARI).

19. The system of claim 15, wherein the rate RPC represents a tachycardia cycle length (TCL) and the stability RPC represents temporal dispersion of local activation recovery interval (ARI).

20. The system of claim 16, wherein the ATP module is configured to deliver only mono-atrial ATP when a correlation of RA to LA activation increases.

21. The system of claim 16, wherein the ATP module is configured to deliver bi-atrial ATP when a frequency of AF decreases and a correlation of RA to LA activation does not increase.

22. The system of claim 16, wherein the NS module is configured to increase the NS therapy when a frequency of AF does not decrease and a correlation of RA to LA activation does not increase.

23. The system of claim 15, wherein:
the measurement module is configured to measure, after delivery of the ATP therapy, post-ATP characteristic values for the rate and stability RPCs;
the analysis module is configured to analyze the post-ATP characteristic values for the rate and stability RPCs for differences, pre-ATP and post-ATP therapy to determine a post-ATP rate RPC difference and a post-ATP stability RPC difference; and
at least one of i) the ATP module is configured to deliver a different ATP therapy and ii) the NS module is configured to deliver a different NS therapy based on the differences in the post-ATP rate RPC difference and the post-ATP stability RPC difference.

24. The system of claim 22, wherein the post-ATP rate RPC represents a frequency of atrial fibrillation (AF) and the post-ATP stability RPC represents correlation of RA to LA activation in time.

* * * * *